US010765355B2

(12) United States Patent
Nelson et al.

(10) Patent No.: US 10,765,355 B2
(45) Date of Patent: Sep. 8, 2020

(54) MONITORING BLADDER DYSFUNCTION USING A PROBABILITY FUNCTION

(71) Applicant: Medtronic, Inc., Minneapolis, MN (US)

(72) Inventors: Dwight E. Nelson, Shoreview, MN (US); Thaddeus S. Brink, St. Paul, MN (US); Lance Zirpel, Lino Lakes, MN (US); Adam P. Steiner, Mankato, MN (US)

(73) Assignee: Medtronic, Inc., Minneapolis, MN (US)

( * ) Notice: Subject to any disclaimer, the term of this patent is extended or adjusted under 35 U.S.C. 154(b) by 196 days.

(21) Appl. No.: 15/964,739

(22) Filed: Apr. 27, 2018

(65) Prior Publication Data

US 2019/0328303 A1    Oct. 31, 2019

(51) Int. Cl.
| | | |
|---|---|---|
| *A61B 5/20* | (2006.01) | |
| *A61N 1/36* | (2006.01) | |
| *G16H 20/40* | (2018.01) | |
| *G16H 50/30* | (2018.01) | |
| *A61B 5/0488* | (2006.01) | |
| *A61B 5/00* | (2006.01) | |

(52) U.S. Cl.
CPC .............. *A61B 5/204* (2013.01); *A61B 5/205* (2013.01); *A61N 1/36007* (2013.01); *A61B 5/04882* (2013.01); *A61B 5/4836* (2013.01); *G16H 20/40* (2018.01); *G16H 50/30* (2018.01)

(58) Field of Classification Search
CPC ....... A61B 5/204; A61B 5/205; A61B 5/4836; A61N 1/36007
USPC .......................................................... 607/41
See application file for complete search history.

(56) References Cited

U.S. PATENT DOCUMENTS

| | | |
|---|---|---|
| 5,416,469 A | 5/1995 | Colling |
| 6,400,982 B2 | 6/2002 | Sweeney et al. |
| 6,678,548 B1 | 1/2004 | Echauz et al. |
| (Continued) | | |

FOREIGN PATENT DOCUMENTS

| | | |
|---|---|---|
| WO | 2010123704 A2 | 10/2010 |
| WO | 2011156288 A2 | 12/2011 |
| WO | 2015013749 A1 | 2/2015 |

OTHER PUBLICATIONS

International Search Report and Written Opinion of International Application No. PCT/US2019/021736, dated May 10, 2019, 13 pp.

*Primary Examiner* — Amanda K Hulbert
*Assistant Examiner* — Philip C Edwards
(74) *Attorney, Agent, or Firm* — Shumaker & Sieffert, P.A.

(57) ABSTRACT

This disclosure describes methods, systems, and devices configured to determine a timing of a future bladder related event of a patient. For example, a system includes processing circuitry configured to identify a timing of a plurality of bladder related events of a patient, determine, based on the timing of the plurality of bladder related events of the patient, a probability to experience a bladder related event function for the patient, the probability to experience a bladder related event function indicating a probability that the patient will experience a bladder related event at an elapsed time after a previous bladder related event, predict, based on the probability to experience a bladder related event function, a timing of a future bladder related event, and control delivery of a therapy to the patient based on the predicted timing of the future bladder related event.

29 Claims, 16 Drawing Sheets

(56) References Cited

U.S. PATENT DOCUMENTS

| | | |
|---|---|---|
| 6,950,704 B1 | 9/2005 | Bradley |
| 7,415,308 B2 | 8/2008 | Gerber et al. |
| 7,580,741 B2 | 8/2009 | Cazares et al. |
| 7,613,516 B2 | 11/2009 | Cohen et al. |
| 7,764,996 B2 | 7/2010 | Zhang et al. |
| 8,209,018 B2 | 6/2012 | Osorio et al. |
| 2006/0020225 A1 | 1/2006 | Gerber et al. |
| 2007/0225616 A1 | 9/2007 | Brown et al. |
| 2007/0255176 A1 | 11/2007 | Rondoni et al. |
| 2007/0255346 A1 | 11/2007 | Rondoni et al. |
| 2008/0058664 A1 | 3/2008 | Mirro |
| 2009/0083070 A1 | 3/2009 | Giftakis et al. |
| 2011/0040546 A1 | 2/2011 | Gerber et al. |
| 2013/0079841 A1 | 3/2013 | Su et al. |
| 2013/0289446 A1* | 10/2013 | Stone .................. A61N 1/3606<br>600/586 |
| 2016/0136420 A1 | 5/2016 | Brink et al. |
| 2017/0065821 A1* | 3/2017 | Brink .................. A61B 5/4836 |

\* cited by examiner

MONITORING BLADDER DYSFUNCTION USING A PROBABILITY FUNCTION

TECHNICAL FIELD

The disclosure relates to medical devices and, more particularly, medical devices that deliver therapy to a patient.

BACKGROUND

Bladder dysfunction, such as overactive bladder, urgency, or urinary incontinence, are problems that may afflict people of all ages, genders, and races. Various muscles, nerves, organs and conduits within the pelvic floor cooperate to collect, store and release urine. A variety of disorders may compromise urinary function, and contribute to an overactive bladder, urgency, urinary incontinence and/or urinary retention. Many of the disorders may be associated with aging, injury, or illness.

Urinary incontinence may include urge incontinence and stress incontinence. In some examples, urge incontinence may be caused by disorders of peripheral or central nervous systems that control bladder micturition reflexes. Some patients may also suffer from nerve disorders that prevent proper triggering and operation of the bladder, sphincter muscles, or nerve disorders that lead to overactive bladder activities or urge incontinence.

Urinary incontinence can be attributed to improper sphincter function, either in the internal urinary sphincter or external urinary sphincter. For example, aging can result in weakened sphincter muscles, which may cause incontinence. Nerves running though the pelvic floor stimulate contractility in the sphincter. An improper communication between the nervous system and the urethra or urinary sphincter can result in a bladder dysfunction, such as overactive bladder, urgency, urge incontinence, or another type of urinary incontinence. Nerve disorders, weakened bladder muscles, or obstructions of a urethra may lead urinary retention, in which the patient is unable to empty their bladder completely.

SUMMARY

In general, the disclosure is directed to techniques and/or systems or devices for identifying and/or treating bladder dysfunction such as urinary incontinence. For example, a system may identify a timing of a plurality of events relating to bladder function of a patient. The system may then determine, based on the timing of the plurality of events relating to bladder function of the patient, a probability to experience a bladder related event function for the patient. The probability to experience a bladder related event function may indicate the probability that the patient will void the bladder or experience another event relating to bladder function, such as, for example, pelvic, groin, or abdominal pain, urinary urge, urgency, urine leakage, or the like at some elapsed time after a previous bladder related event. In this manner, the system may use the probability to experience a bladder related event function to predict a timing of a future bladder related event of the patient. In turn, the system may employ a probability to experience a bladder related event function to control at least one of a timing of delivery of therapy to the patient or therapy parameter values of the therapy. In some examples, the system may be configured to detect a urinary condition of the patient, determine the efficacy of a therapy delivered to the patient, modify one or more therapy parameter values of the therapy delivered to the patient, or combinations thereof. In some examples, the probability to experience a bladder related event function may be a probability to void function that indicates the probability that the patient will void the bladder.

In one example, a method includes identifying a timing of a plurality of bladder related events of a patient, determining, based on the timing of the plurality of bladder related events of the patient, a probability to experience a bladder related event function for the patient, the probability to experience a bladder related event function indicating a probability that the patient will experience a bladder related event at an elapsed time after a previous bladder related event, predicting, based on the probability to experience a bladder related event function, a timing of a future bladder related event, and controlling delivery of a therapy to the patient based on the predicted timing of the future bladder related event.

In another example, a system includes processing circuitry configured to identify a timing of a plurality of bladder related events of a patient, determine, based on the timing of the plurality of bladder related events of the patient, a probability to experience a bladder related event function for the patient, the probability to experience a bladder related event function indicating a probability that the patient will experience a bladder related event at an elapsed time after a previous bladder related event, predict, based on the probability to experience a bladder related event function, a timing of a future bladder related event, and control delivery of a therapy to the patient based on the predicted timing of the future bladder related event.

In another example, a computer readable storage medium includes instructions that, when executed, causes processing circuitry to identify a timing of a plurality of bladder related events of a patient, determine, based on the timing of the plurality of bladder related events of the patient, a probability to experience a bladder related event function for the patient, the probability to experience a bladder related event function indicating a probability that the patient will experience a bladder related event at an elapsed time after a previous bladder related event, predict, based on the probability to experience a bladder related event function, a timing of a future bladder related event, and control delivery of a therapy to the patient based on the predicted timing of the future bladder related event.

The details of one or more examples of the disclosure are set forth in the accompanying drawings and the description below. Other features, objects, and advantages of the disclosure will be apparent from the description and drawings, and from the claims.

DETAILED DESCRIPTION

Figure 1:
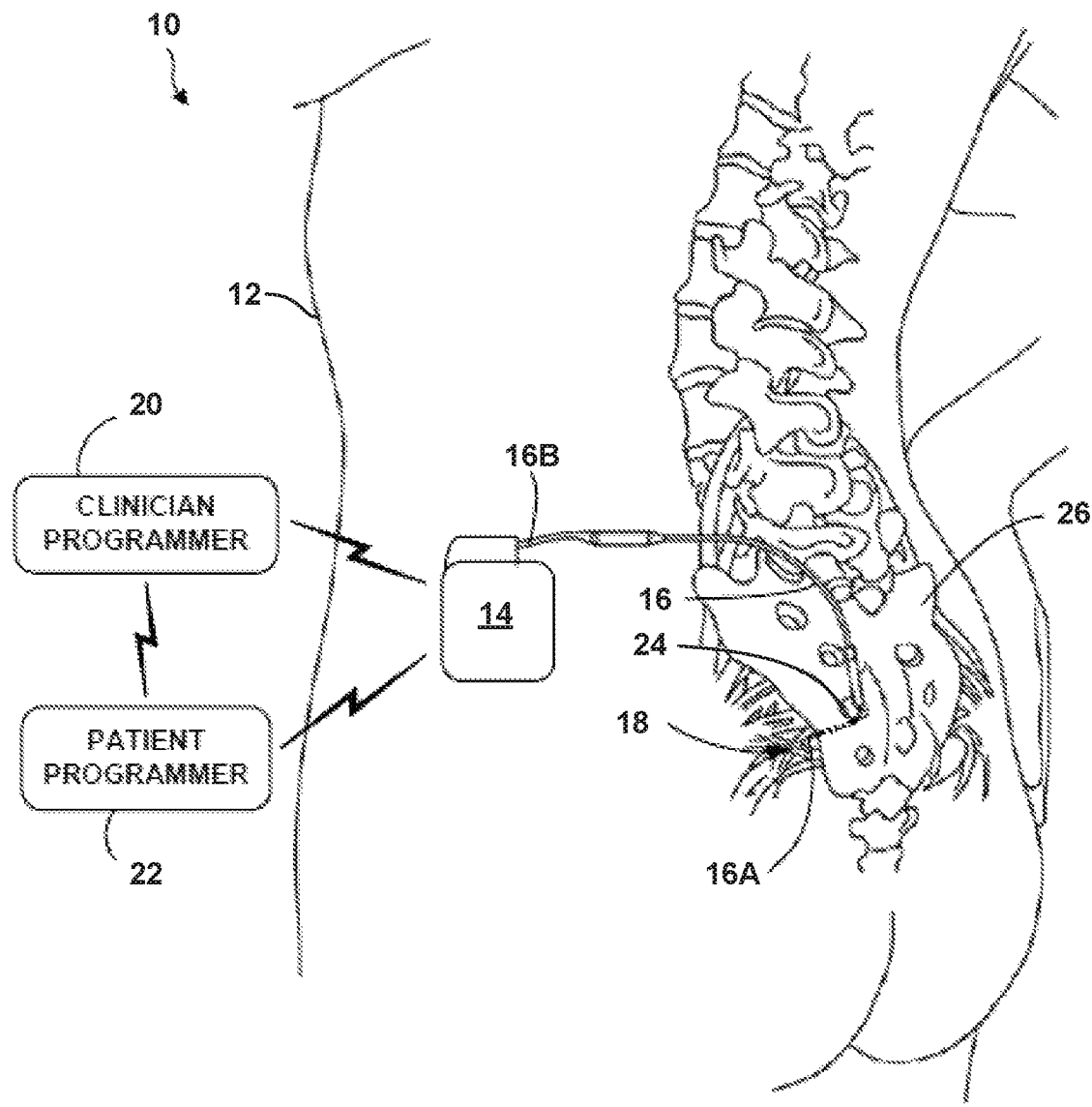
FIG. 1 is conceptual diagram illustrating an example system configured to determine a probability to experience a bladder related event function for a patient.

The disclosure is directed to techniques, systems, and devices configured to determine a probability to experience a bladder related event function for a patient based on a timing of a plurality of events related to bladder function and predict a future event related to bladder function based on the probability to experience a bladder related event function. In some examples, a system may use the probability to experience a bladder related event function to control delivery of therapy to a patient and/or deliver the therapy to a patient. For example, the system may use the probability to experience a bladder related event function to control delivery therapy to a patient to treat bladder dysfunction experienced by the patient. Bladder dysfunction generally refers to a condition of improper functioning of the bladder or urinary tract, and may include, for example, an overactive bladder, urgency, urinary incontinence, and/or urinary retention. Urgency is a sudden, compelling urge to urinate, and may often, though not always, be associated with urinary incontinence. Overactive bladder may include excessive contractions of the detrusor muscle (e.g., smooth muscle residing in the wall of the bladder) and may be one of the causes for urgency. Urinary incontinence refers to a condition of involuntary loss of urine, and may include urge incontinence, stress incontinence, or both stress and urge incontinence, which may be referred to as mixed urinary incontinence. As used in this disclosure, the term "urinary incontinence" includes disorders in which urination occurs when not desired, such as stress or urge incontinence (e.g., overactive bladder). Urinary retention refers to a condition in which a patient is unable to empty their bladder completely.

In order to void urine, the nervous system and several muscles of the body typically work in concert to expel urine from the bladder. For example, the internal urinary sphincter muscle and the external urinary sphincter muscle relax to allow urine to pass through the openings in these sphincters. In addition, the detrusor muscle in the wall of the bladder contracts to increase the internal bladder pressure and force urine out of the bladder and through the urethra and past the urinary sphincters. Bladder dysfunction can occur when portions of the nervous system that innervate these muscles, or the muscles themselves, prevent the patient from retaining urine until the patient voluntarily decides to urinate.

For example, urge incontinence may be caused by disorders of peripheral or central nervous systems that control bladder micturition reflexes. Some patients may also suffer from nerve disorders that prevent proper triggering and operation of the bladder, sphincter muscles or nerve disorders that lead to overactive bladder activities or urge incontinence. Additionally, or alternatively, urinary incontinence can be attributed to improper sphincter function, either in the internal urinary sphincter or external urinary sphincter. In some examples, aging can result in weakened sphincter muscles, which may cause incontinence. Nerves running though the pelvic floor stimulate contractility in the sphincter. An improper communication between the nervous system and the urethra or urinary sphincter can result in a bladder dysfunction, such as overactive bladder, urgency, urge incontinence, urinary retention, or another type of urinary condition.

Some treatments for urinary conditions such as overactive bladder or urge incontinence may be based on a volume of a bladder of a patient and/or a pressure of the bladder of the patient. In some examples, however, the volume and/or pressure of the bladder of the patient may be difficult to determine, or difficult to determine accurately. Moreover, determining the volume or pressure of the bladder of the patient may require implantation of one or more invasive sensors within the body of the patient to detect the volume or the pressure of the bladder. In some cases, therapy delivered to the patient based on such volume or pressure measurements alone may be less efficacious than some therapies based on other parameters because of the difficulty of accurately detecting the volume or pressure of the bladder.

As described in this disclosure, various techniques and systems may be used to identify a timing of a plurality of bladder related events of a patient and determine, based on the timing of the plurality of bladder related events of the patient, a probability to experience a bladder related event function for the patient. The probability to experience a bladder related event function may be used by a system to predict a timing of a future bladder related event. The probability to experience a bladder related event function or the predicted timing of the future bladder related event can be used to deliver therapy to a patient, adjust one or more therapy parameter values that define therapy delivered to the patient, control delivery of therapy to the patient, determine the efficacy of therapy delivered to the patient, modify therapy delivered to the patient over time, detect a urinary condition of the patient, and/or the like. In some examples, the bladder related event may include a void event and/or one or more symptoms relating to bladder function of a patient, such as, for example, leakage of urine, a sensation of pain or a similar perception in the pelvic and/or abdominal areas, a sensation of urge, urgency, suddenly needing to void or rapidly seeking a location to void, or combinations thereof.

In some examples, the timing of the plurality of bladder related events may be less complicated to determine than a volume or a pressure of the bladder of the patient. Additionally, or alternatively, to being less complicated to determine, the timing of the plurality of bladder related events may be able to be determined more accurately than the volume or pressure of the bladder of the patient. In this way, a system may be able to deliver more efficacious therapy to the patient with better information regarding the fill status of the bladder, may be able to deliver therapy for a longer amount of time, may be able to monitor the bladder dysfunction of the patient over time (e.g., with or without therapy delivered during this time), or compare therapy efficacy to other therapies, such as those based on a volume or a pressure of the bladder of the patient.

FIG. 1 is conceptual diagram illustrating an example system 10 configured to determine a probability to experience a bladder related event function for a patient 12. Patient 12 ordinarily will be a human patient. In some cases, however, system 10 may be applied to other mammalian or non-mammalian, non-human patients. In some examples, patient 12 experiences bladder dysfunction, such as, for example, improper functioning of a bladder, a urinary sphincter, or a urinary tract, and may include an overactive bladder, urgency, urinary incontinence, urinary retention, or combinations thereof.

System 10 is configured to identify a timing of a plurality of bladder related events of patient 12. For example, patient 12 may input the timing of a voiding event or another bladder related event using a user input device (e.g., enter the times at which voiding events or other bladder related events happen or have happened), such as a patient programmer 22. In some such examples, patient 12 may not need an additional, invasive medical device or sensor implanted with the body of patient 12 to identify the plurality of bladder related events. Instead, patient 12 may be able to use patient programmer 22 or another user interface device to input the timing of a bladder related event to create a patient-entered log of bladder related events. For example, patient 12 may be able to input that a voiding event is occurring, a voiding event occurred, or that a voiding event is about to occur. In other examples, patient 12 may input one or more additional or alternative bladder related events, such as pain, urge, urgency, leakage, or the like. When the patient enters the bladder related event in real-time, patient programmer 22 may add a time stamp to the entry to automatically track the time of the bladder related event. In some examples, patient 12 may be able to input additional information about the bladder related event, such as a time when the bladder related event occurred (e.g., when the bladder related event has occurred in the past), whether the bladder related event was voluntary or involuntary, an approximation of the amount of urine that was voided during the voiding event (e.g., in the case of the bladder related event being a void event), or the like.

In some examples, system 10 may include one or more sensors configured to identify the timing of a plurality of bladder related events of patient 12 in addition to, or as an alternative to, input from patient 12. For example, system 10 may include a sensor configured to determine a volume of the bladder of patient 12, a sensor configured to determine a pressure of the bladder, a sensor configured to detect that fluid has been voided from patient 12, or the like. Such sensors may be able to identify the timing of the plurality of bladder related events by comparing the volume and/or pressure to predetermined threshold value, by comparing the volume and/or pressure to a previous volume and/or pressure value, for example. In some examples, the one or more sensors may be included in an implantable medical device (IMD) 14 or a lead 16 of the IMD 14. In other examples, the one or more sensors may be separate from IMD 14 and/or lead 16, but may be in communication, e.g., via a network and/or direct wireless communication, with IMD 14, lead 16, patient programmer 22, or a clinician programmer 20.

In addition to, or as an alternative to, one or more sensors to detect a pressure and/or a volume of the bladder of patient 12, system 10 may include a sensor configured to detect a physical activity of patient 12. For example, a sensor may be configured to detect a posture, a movement, or an activity level. The physical activity may be used to identify a timing of a bladder related event. For example, a sudden movement of patient 12 from a lying down or relaxed position to an upright or standing position may indicate that patient 12 is experiencing a bladder related event. In another example, fidgeting of the patient followed by a period of non-motion may indicate that a bladder related event has occurred. The sensor configured to detect a physical activity of patient 12 may include one or more accelerometers, a set of electrodes, a temperature sensor, or another sensor that is configured to detect a physical activity of patient 12. The sensor may be included in IMD 14 and/or lead 16, or may be separate from IMD 14 and/or lead 16 and in communication, e.g., via a network or direct communication, with IMD 14, lead 16, patient programmer 22, or clinician programmer 20.

In some cases, the timing of the plurality of bladder related events may be identified by a manner other than, or in addition to, input from patient 12 and/or by one or more sensors. For example, system 10 may use a geofence to determine the timing of a bladder related event, such as a voiding event, of patient 12. System 10 may establish a geographical boundary (e.g., geofence) around a bathroom, a toilet, or the like based on geographical positioning system (GPS), radio frequency identification (RFID) information, another range detecting technology, or any combination thereof. A device, such as patient programmer 22, may be able to determine when patient 12 is within the geofence via GPS or RFID information. If it is determined that patient 12 is within the identified geofence, patient programmer 22 may identify that a voiding event or another bladder related event has occurred based on patient 12 being within the geofence. In some examples, patient 12 may be able to input additional information and/or edit the identified bladder related events. As one example, patient 12 may be able to delete an identified bladder related event in the case in which patient 12 entered the geofenced area for a reason other than for a bladder related event. As another example, patient 12 may be able to add a bladder related event in the case patient 12 experienced the bladder related event somewhere other than the geofenced area. In this manner, patient programmer 22 may prompt the user to confirm that a bladder related event has occurred in response to detecting that patient 12 was located within the identified geofence area.

In some examples, identifying a timing of a plurality of bladder related events of patient 12 may include identifying the timing of the plurality of bladder related events over a predetermined amount of time. For example, the timing of the plurality of bladder related events of patient 12 may be identified over a predetermined time period of a day (e.g., a specific hour duration, day, or night), a few days, a week, or a month. In other examples, the timing of the plurality of bladder related events of patient 12 may be identified over a different predetermined time period.

System 10 may also be configured to determine a probability to experience a bladder related event function for patient 12 based on the timing of the plurality of bladder related events of patient 12. In some examples, IMD 14, patient programmer 22, and/or clinician programmer 20 may determine the probability to experience a bladder related event function for patient 12. In other examples, one or more remote devices (such as a networked server) may be configured to determine a probability to experience a bladder related event function for patient 12 based on received data representative of the timing of the plurality of bladder related events of patient 12.

The probability to experience a bladder related event function may be represented in different ways, such as an instantaneous probability to experience a bladder related event function or a cumulative probability to experience a bladder related event function that indicates a probability that patient 12 will experience a bladder related event at an elapsed time after a previous bladder related event. An instantaneous probability to experience a bladder related event function indicates the probability that patient 12 will experience a bladder related event at any given time after a previous void event. The instantaneous probability to experience a bladder related event function may take into account the probability of whether patient 12 has experienced a subsequent bladder related event since the previous bladder related event. For example, an instantaneous probability to experience a bladder related event function may indicate the probability that patient 12 will experience a bladder related event at a first amount of time after a previous bladder related event is about 40%. The instantaneous probability to experience a bladder related event function may also indicate that the probability that patient 12 will experience a bladder related event at a second amount of time, greater than the first amount of time, after the previous bladder related event as close to 0% because it is likely patient 12 has already had a subsequent bladder related event after the previous bladder related event. In this manner, the instantaneous probability to experience a bladder related event function may indicate an increasing likelihood of experiencing a bladder related event at first and then a decreasing likelihood of experiencing another bladder related event as the time extends further from the previous bladder related event.

A cumulative probability to experience a bladder related event function indicates the probability that patient 12 will experience a bladder related event at a certain amount of time after a previous bladder related event to indicate the probability that the patient has experienced a bladder related event at any time after the previous bladder related event. For example, a cumulative probability to experience a bladder related event function may indicate the probability that patient 12 will experience a bladder related event at a first amount of time after a previous bladder related event is about 40%. The cumulative probability to experience a bladder related event function may also indicate that the probability that patient 12 will experience a bladder related event at a second amount of time, greater than the first amount of time, after the previous bladder related event as close to 100% since the cumulative probability to experience a bladder related event function assumes that patient 12 has yet to have a subsequent bladder related event. In this manner, the cumulative probability to experience a bladder related event function continues to increase the probability that the patient has experienced a bladder related event as the time from the last bladder related event increases.

In some examples, system 10 may determine the probability to experience a bladder related event function based on a plurality of subjects instead of a single patient. This probability to experience a bladder related event function that is based on the plurality of subjects may be referred to as a composite probability to experience a bladder related event function because it is generated based on more than one subject. A composite probability to experience a bladder related event function may also be represented as either an instantaneous probability to experience a bladder related event function or a cumulative probability to experience a bladder related event function. For example, system 10 may select or determine a probability to experience a bladder related event function based on a plurality of subjects and based on one or more parameters of patient 12 and/or the plurality of subjects. In some cases, the composite probability to experience a bladder related event function based on a plurality of subjects may be determined using subjects selected based on an age of patient 12, a gender of patient 12, and/or a body composition of patient 12. As one example, the composite probability to experience a bladder related event function based on a plurality of subjects may be determined such that the age of patient 12, the gender of patient 12, and/or the body composition of patient 12 is similar to that of the plurality of subjects. In some examples, one or more of the plurality of subjects may experience bladder dysfunction. For example, in some cases, all of the plurality of subjects may experience bladder dysfunction. In other examples, the plurality of subjects may not experience bladder dysfunction (e.g., have normal bladder function).

System 10 may adjust the composite probability to experience a bladder related event function based on the timing of the plurality of bladder related events of the specific patient 12. For example, the composite probability to experience a bladder related event function based on the plurality of subjects that have normal bladder function may be adjusted to better fit the timing of the bladder related events experienced by patient 12 (e.g., exhibiting bladder dysfunction). In some examples, the composite probability to experience a bladder related event function based on the plurality of subjects may shifted in time, narrowed or widened, decreased or increased in amplitude, or the like to be adjusted based on the timing of the plurality of bladder related events of patient 12.

Additionally, or alternatively, determining the probability to experience a bladder related event function for patient 12 may be based on at least one of a pressure of the bladder of patient 12, a volume of the bladder of patient 12, a physical activity of patient 12, a time of day, an amount of fluid intake of patient 12, or an amount of caffeine consumed by patient 12. In some examples, the pressure of the bladder, the volume of the bladder, or the physical activity may be determined by one or more sensors, as described above. Similarly, the time of day, the amount of fluid intake, or the amount of caffeine consumed by patient 12 may be determined by a sensor, either internal or external to patient 12.

In other examples, any of the pressure of the bladder, the volume of the bladder, the physical activity, the time of day, the amount of fluid intake, or the amount caffeine consumed may be determined by a user interface device, such as patient programmer 22. For example, patient 12 may use patient programmer 12 to input the physical activity, the time of day, the amount of fluid intake, and/or the amount caffeine consumed. As another example, patient programmer 22 may be able to determine the pressure of the bladder, the volume of the bladder, the physical activity, the time of day, the amount of fluid intake, and/or the amount caffeine consumed without input from patient 12. For example, patient programmer 22 may include a built-in clock to determine the time of day.

In some examples, determining the probability to experience a bladder related event function for patient 12 based on at least one of a pressure of the bladder of patient 12, a volume of the bladder of patient 12, a physical activity of patient 12, a time of day, an amount of fluid intake of patient 12, or an amount of caffeine consumed by patient 12 may include shifting a probability to experience a bladder related event function in time, narrowing or widening the time aspect of the probability to experience a bladder related event function, decreasing or increasing the probability to experience a bladder related event function in amplitude, or the like. For example, an amount of fluid intake greater than a predetermined threshold or greater than a previous or average amount of fluid intake may result in the probability to experience a bladder related event function being adjusted to indicate shorter times from a previous bladder related event resulting in a higher probability of a future bladder related event in comparison to a probability to experience a bladder related event function based on a smaller amount of fluid intake. In this manner, system 10 may be configured to adjust the probability to experience a bladder related event function based on inputs indicative of patient activity.

In some examples, the probability to experience a bladder related event function may be adjusted based on an advancing age of patient 12 and/or advancing bladder dysfunction of patient 12. For example, adjusting the probability to experience a bladder related event function may include shifting a probability to experience a bladder related event function in time, narrowing or widening the time aspect of the probability to experience a bladder related event function, decreasing or increasing the probability to experience a bladder related event function in amplitude, or the like. In some examples, an aging patient may result in the probability to experience a bladder related event function being adjusted to indicate shorter times from a previous bladder related event resulting in a higher probability of a future bladder related event in comparison to a probability to experience a bladder related event function based on a younger patient. A similar adjustment may be made for patient 12 with advancing bladder dysfunction in comparison to a patient with bladder dysfunction remaining relatively constant or improving.

System 10 is also configured to determine a timing of a future bladder related event based on the probability to experience a bladder related event function for patient 12. For example, an instantaneous probability to experience a bladder related event function or a cumulative probability to experience a bladder related event function may indicate the timing of a future bladder related event based on the probability a future bladder related event will occur from an occurrence of a previous bladder related event. In some examples, determining the timing of the future bladder related event may be used to control delivery of therapy to patient 12. For example, patient programmer 20, patient programmer 22, or IMD 14 may be configured to control delivery of a therapy to patient 12 based on the predicted timing of the future bladder related event. Delivery of therapy to patient 12 based on the predicted timing of the future bladder related event will be described in more detail below.

IMD 14 may provide electrical stimulation therapy to target tissue site 18 located proximate a sacral nerve, a pudendal nerve, a hypogastric nerve, a pelvic nerve, an afferent nerve, or another nerve associated with the bladder of patient 12 by generating a programmable electrical stimulation signal (e.g., in the form of electrical pulses) and delivering the electrical stimulation signal to target tissue site 18 via lead 16. In some examples, lead 16 includes one or more stimulation electrodes disposed on distal end 16A of lead 16 and implanted proximate to target tissue site 18 such that the electrical stimulation is delivered from IMD 14 to target tissue site 18 via the stimulation electrodes. The electrical stimulation therapy may be used to treat bladder dysfunction of patient 12.

In general, the sacral nerves include five sacral nerves that emerge from the sacrum. In some examples, the sacral vertebrae (S1-S5) may be used to number the sacral nerves. The sacral nerves contribute to the sacral plexus (a network of intersecting nerves that innervates the posterior thigh, part of the lower leg, the foot, and part of the pelvis) and the coccygeal plexus (a network of intersecting nerves near the coccyx bone, e.g., the tailbone, that innervates the skin of the coccyx bone and around the anus). In general, the pudendal nerve is a somatic nerve in the pelvic region, which is a large branch of the sacral plexus. The pudendal nerve innervates the external genitalia, the urinary sphincters, and the anal sphincters. The hypogastric nerves and pelvic nerves innervate the detrusor muscle of the bladder. The afferent nerves are sensory nerves that include stretch receptors of the bladder, and may send signals to the brain of patient 12 that may result in increased activity of the detrusor muscle of the bladder.

As illustrated in the example of FIG. 1, distal end 16A of lead 16 is implanted proximate to target tissue site 18. In the example shown in FIG. 1, target tissue site 18 is proximate the S3 sacral nerve of patient 12. In this example, in order to implant distal end 16A of lead 16 proximate to the S3 sacral nerve, lead 16 may be introduced into the S3 sacral foramen 24 of sacrum 26 to access the S3 sacral nerve. For some patients, stimulation of the S3 sacral nerve may be effective in treating bladder dysfunction of patient 12. In other examples, distal end 16A may be implanted proximate to a different target tissue site, such as a target tissue site proximate to a different sacral nerve, a pudendal nerve, a hypogastric nerve, a pelvic nerve, an afferent nerve, or another nerve associated with the bladder of patient 12 to treat the bladder dysfunction of patient 12.

Although FIG. 1 illustrates one lead 16, in some examples, IMD 14 may be coupled to two or more leads, e.g., to facilitate bilateral or multi-lateral stimulation. In some examples, lead 16 may also carry one or more sense electrodes via which IMD 14 can sense one or more physiological parameters (e.g., nerve signals, EMG, or the like) of patient 12, in addition to the one or more stimulation electrodes carried by lead 16. In some examples, lead 16 includes a lead body, and proximal end 16B of lead 16 may be electrically coupled to IMD 14 via one or more conductors extending substantially through the lead body between the one or more stimulation electrodes carried by lead 16 and IMD 14.

In the example shown in FIG. 1, lead 16 is cylindrical. One or more electrodes of lead 16 may be ring electrodes, segmented electrodes, or partial ring electrodes. Segmented or partial ring electrodes each extend along an arc less than 360 degrees (e.g., 70-120 degrees) around the outer perimeter of the lead 16, where in some example, multiple electrode segments are disposed around the perimeter of lead 16 at the same axial position of lead 16. In some examples, segmented electrodes may be useful for targeting different fibers of the same or different nerves to generate different physiological effects or for delivering relatively higher frequency stimulation (e.g., about 66 Hertz) and relatively lower frequency stimulation (e.g., about 15 Hertz) to activate both fast twitch muscles and slow twitch muscles substantially simultaneously or at alternating time slots. In some examples, lead 16 may be, at least in part, paddle-shaped (e.g., a "paddle" lead) with a flat or curved surface.

In some examples, one or more of the electrodes of lead 16 may be cuff electrodes that are configured to extend at least partially around a nerve (e.g., extend axially around an outer surface of a nerve). In some cases, delivering stimulation via one or more cuff electrodes and/or segmented electrodes may help achieve a more uniform electrical field or activation field distribution relative to the nerve in some examples, which may help minimize discomfort to patient 12 that results from the delivery of electrical stimulation. An electrical field represents the areas of a patient anatomical region that are covered by an electrical field during delivery of electrical stimulation to tissue within patient 12. The electrical field may define the volume of tissue that is affected when the electrodes of lead 16 are activated. An activation field represents the neurons that will be activated by the electrical field in the neural tissue proximate to the activated electrodes.

The illustrated numbers and configurations of lead 16 and electrodes carried by lead 16 are merely one example. Different configurations, e.g., different quantities and/or positions of leads and electrodes, are possible. For example, in other examples, IMD 14 may be coupled to additional leads or lead segments having one or more electrodes positioned at different locations in the pelvic region of patient 12. In some examples, lead 16 may have two electrodes, three electrodes, four electrodes, or eight electrodes. In other examples, lead 16 may have a combination of ring electrodes and segmented electrodes.

IMD 14 may be surgically implanted in patient 12 at any suitable location within patient 12, such as within in an abdomen of patient 12. In some examples, the implantation site may be a subcutaneous location in the side of the lower abdomen or the side of the lower back or upper buttocks. IMD 14 has a biocompatible outer housing, which may be formed from titanium, stainless steel, a liquid crystal polymer, or the like. In some examples, electrical conductors disposed within the lead body of lead 16 electrically connect electrodes to an electrical stimulation delivery module within IMD 14. In other examples, system 10 may include a leadless electrical stimulator, such as a microstimulator (e.g., a capsule shaped microstimulator), where the leadless electrical stimulator delivers electrical stimulation to target tissue site 18. Although IMD 14 is generally described as delivering electrical stimulation therapy, IMD 14 may alternatively, or additionally, deliver other therapies such as drug delivery therapy and/or ultrasound therapy.

In the example illustrated in FIG. 1, system 10 includes clinician programmer 20 and patient programmer 22. In some examples, one or both programmers 20 and 22 may be wearable communication devices integrated into a key fob or a wrist watch. In other examples, one or both programmers 20 and 22 may be handheld computing devices, computer workstations, or networked computing devices. Programmers 20 and 22 may include respective user interfaces that receive input from a user (e.g., a clinician or patient 12, respectively). The user interfaces may include components for interaction with a user, such as a keypad and a display. In some examples, the display may be a cathode ray tube (CRT) display, a liquid crystal display (LCD), or light emitting diode (LED) display and the keypad may take the form of an alphanumeric keypad or a reduced set of keys associated with particular functions. Programmers 20 and 22 can, additionally or alternatively, include a peripheral pointing device, e.g., a mouse, via which a user may interact with the user interface. In some examples, the displays may include a touch screen display, and a user may interact with programmers 20 and 22 via the touch screens of the displays. In some examples, the user may also interact with programmers 20 and 22 and/or IMD 14 remotely via a networked computing device.

Clinician programmer 20 facilitates interaction of a clinician with one or more components of system 10. In some examples, the clinician, (e.g., physician, technician, surgeon, electrophysiologist, or other clinician) may interact with clinician programmer 20 to communicate with IMD 14. For example, the clinician may retrieve physiological or diagnostic information from IMD 14 via clinician programmer 20. As another example, the clinician may interact with programmer 20 to program IMD 14, e.g., select values that define electrical stimulation generated and delivered by IMD 14, select other operational parameters of IMD 14, or the like. As another example, the clinician may use programmer 20 to retrieve information from IMD 14 regarding the performance or integrity of IMD 14 or other components of system 10, such as lead 16 or a power source of IMD 14. In some examples, this information may be presented to the clinician as an alert if a system condition that may affect the efficacy of therapy is detected.

In some examples, a clinician may use clinician programmer 20 to create stimulation programs for electrical stimulation (generated and delivered by IMD 14) as therapy to treat bladder dysfunction of patient 12. In some examples, the clinician programmer 20 transmits the stimulation programs to IMD 14 for storage in a memory of IMD 14. Clinician programmer 20 may also allow the clinician to access one or more probability to experience a bladder related event functions for patient 12. In some examples, clinician programmer 20 enables the clinician to transmit one or more probability to experience a bladder related event functions to IMD 14, such as a composite probability to experience a bladder related event function based on a plurality of subjects that is used to determine a probability to experience a bladder related event function for patient 12. In this manner, clinician programmer 20 may be configured to have additional functionality and/or control of IMD 14 than patient programmer 22.

Patient programmer 22 facilitates interaction of patient 12 with one or more components of system 10. In some examples, patient 12 may interact with patient programmer 22 to control IMD 14 to deliver electrical stimulation, to manually abort the delivery of electrical stimulation by IMD 14, or to inhibit the delivery of electrical stimulation by IMD 14. Patient 12 may, for example, use a keypad or touch screen of programmer 22 to cause IMD 14 to deliver electrical stimulation, e.g., to activate one or more stimulation programs, or the like.

In some examples described herein, patient 12 may provide input to patient programmer 22 indicating that a bladder related event occurred. For example, in some examples, patient 12 may select a particular button of patient programmer 22 to indicate an occurrence of a bladder related event or provide input to a touch screen of patient programmer 22 indicating the occurrence of the bladder related event. The button can be a dedicated button that is designated to receive input from patient 12 indicating the bladder related event, or the button can be a multifunction button, such as a soft key that changes function depending upon the section of the user interface currently viewed by patient 12 (or another user). After receiving the input, patient programmer 22 may store the occurrence of the bladder related event, transmit the indication of the bladder related event to IMD 14, identify a timing of a plurality of bladder related events based on the bladder related event, or the like.

In other examples, one or more other components of therapy system 10 receives the patient input indicating the bladder related event. For example, in some examples, patient 12 interacts with IMD 14 to provide the input. As an example, IMD 14 can include a motion sensor integrated into or on a housing of IMD 14, where the motion sensor is configured to generate a signal that is indicative of patient 12 tapping IMD 14 through the skin. The number, rate, or pattern of taps may be associated with the different types of input, such as input indicating a bladder related event occurred, input indicating an intent to void, or the like. Patient 12 may provide the input by tapping IMD 14 and processing circuitry of IMD 14 may identify the tapping of IMD 14 by patient 12 to determine when patient input is received and to identify a timing of a plurality of bladder related events based upon receiving the patient input.

In some examples, it may be desirable to balance the repetitiveness of the therapy with muscle recovery times in order to help prevent muscle fatigue from the stimulation. In some examples, IMD 14 delivers multiple sessions of electrical stimulation daily or over another period of time, multiple cycles of electrical stimulation per session. During each stimulation session, IMD 14 may generate and deliver stimulation according to predetermined therapy programs. In some examples, patient 12 may determine when the delivery of electrical stimulation may be convenient, e.g., not disruptive, not embarrassing, r the like, for patient 12 and may provide input to patient programmer 22 to define the schedule of electrical stimulation delivery to accommodate these times, or provide input to patient programmer 22 that initiates the electrical stimulation delivery accordingly.

IMD 14, clinician programmer 20, and patient programmer 22 may communicate via wireless communication using any techniques known in the art. Examples of communication techniques may include, for example, low frequency or radiofrequency (RF) telemetry. Other techniques are also contemplated. In some examples, clinician programmer 20 and/or patient programmer 22 may include a programming head that may be placed proximate to the patient's body near the IMD 14 implant site in order to improve the quality or security of communication between IMD 14 and clinician programmer 20 and/or patient programmer 22.

Figure 2:
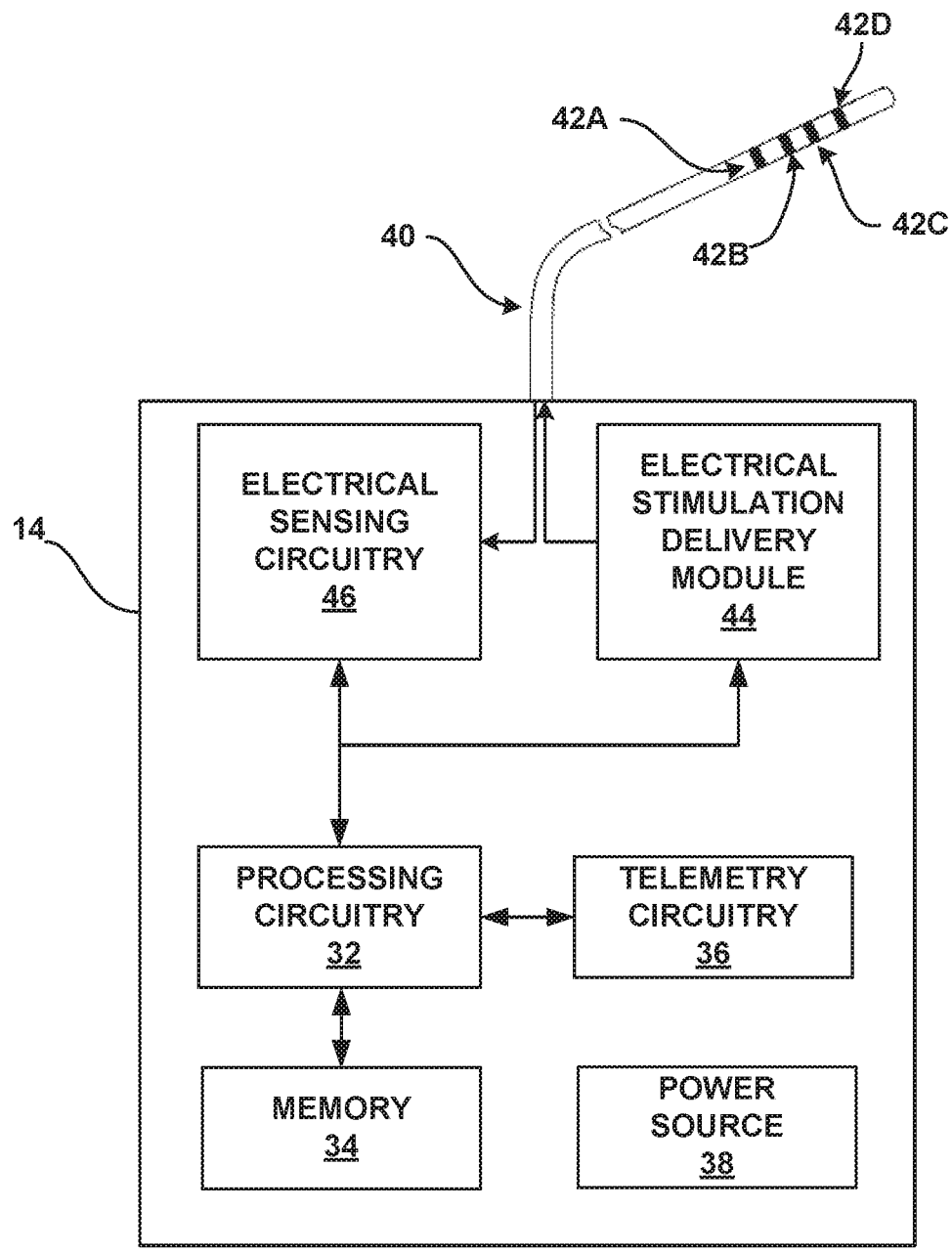
FIG. 2 is a conceptual block diagram illustrating an example of an IMD configured to deliver therapy to a patient.

FIG. 2 is a conceptual block diagram illustrating an example of an IMD 14 configured to deliver therapy to a patient. As shown in FIG. 2, an electrical stimulation delivery module 44 (e.g., electrical circuitry that may include a stimulation generator) of IMD 14 may generate electrical stimulation according to a plurality of electrical stimulation parameter sets or therapy programs. IMD 14 may deliver therapy to one or more nerve fibers of patient 12 via one or more electrodes 42A-D (collectively, "electrodes 42") positioned along lead 40. In some examples, IMD 14 may further include electrical sensing circuitry 46 for sensing a signal generated by one or more of nerve fibers or one or more muscles in response to the electrical stimulation. The same or different electrodes may be used to generate stimulation and detect the response signal. In some examples, different sets of electrodes may be used to deliver stimulation and sense a physiological response to the delivered stimulation. IMD 14 may further include processing circuitry 32 that controls the operations of IMD 14 with the aid of instructions associated with program information that is stored in memory 34. IMD 14 may communicate with an external clinician programmer 20, external patient programmer 22, or another external device via telemetry circuitry 36.

Processing circuitry 32 may include one or more processors, such as microprocessors, digital signal processors (DSPs), application specific integrated circuits (ASICs), field programmable gate arrays (FPGAs), or any other equivalent integrated or discrete logic circuitry, as well as any combinations of such components. Memory 34 may include memory, such as random access memory (RAM), read only memory (ROM), programmable read only memory (PROM), erasable programmable read only memory (EPROM), electronically erasable programmable read only memory (EEPROM), flash memory, comprising executable instructions for causing the one or more processors to perform the actions attributed to them. Further, memory 34 may be implanted entirely in hardware, software, or a combination thereof.

In some examples, processing circuitry 32 of IMD 14 is configured to identify a timing of a plurality of bladder related events of a patient, determine a probability to experience a bladder related event function for the patient based on the identified timing of the plurality of bladder related events of the patient, and predict a timing of a future bladder related event based on the probability to experience a bladder related event function. Processing circuitry 32 may also control delivery of a therapy to the patient based on the predicted timing of the future bladder related event.

In some examples, IMD 14 may possess one or more electrodes 42 coupled to IMD 14 via one or more leads 40. Electrodes 42 may be configured to deliver electrical stimulation according to a plurality of electrical stimulation parameter sets or therapy programs generated by processing 32 and stored in memory 34. Electrodes 42 may operate as a cathode or an anode. Electrodes 42 may be any type of electrode, such as a ring electrode, paddle electrode, cuff electrode, needle electrode, or plate electrode. Electrodes 42 are typically implanted electrodes disposed internal of the patient. However, one or more of electrodes 42 may be external to the patient in some examples. In some examples, Electrodes 42 may be implanted adjacent to or even coupled to one or more of a patient's nerve fibers. In some examples, electrode 42 may be implanted adjacent to or even coupled to (e.g., implanted at least partially within) a tissue or muscle fiber. In some examples, more than one electrode may be coupled to the same nerve. In some examples, electrodes 42 may be coupled to a bundle of nerves or muscle fibers. Although four electrodes 42 are shown in the example of FIG. 2, fewer than four or more than four electrodes may be carried by lead 40, or multiple leads, in other examples. In some examples, some of electrodes 42 may be positioned to deliver stimulation while other electrodes 42 may be positioned to detect physiological responses from delivered stimulation. In other examples, the same electrodes that delivered stimulation may be used to detect nerve and/or muscle responses evoked from the delivered stimulation in order to titrate stimulation.

Each electrical stimulation parameter set or therapy program generated by processing circuitry 32 may define an electrical stimulation signal deliverable to a patient. In some examples, the electrical stimulation parameter set or therapy program may include values for voltage or current amplitude, pulse frequency, pulse width, and/or electrode combination. These values of the voltage or current amplitude over time for each pulse may define the waveshape of each pulse or signal (e.g., rectangular, sinusoidal, Gaussian, sawtooth, rising, falling, etc.). In addition, each stimulation parameter set may define a burst of pulses and a frequency of the burst of pulses instead of a continuous pulse train. Different stimulation parameter sets or therapy programs may vary by a different value for at least one of the stimulation parameters. In some examples, the electrical stimulation parameter may set or therapy program may include the number of pulses or signals or the duration for which pulses are to be delivered. The electrode combination may define which electrodes are used to deliver stimulation signals and the polarity (cathode or anode) of each electrode. In some examples, the electrical stimulation parameter set may define electrical stimulation below a perception threshold (e.g., the level at which the stimulation is perceived by the patient), a motor threshold (e.g., the level at which a muscle response is induced), and/or an activation threshold (e.g., the level at which the nerve is depolarized to activate the nerve) of the patient.

In one example of the system described herein, processing circuitry 32 may select an electrical stimulation parameter set (e.g., values for respective parameters) or therapy program based on a probability to experience a bladder related event function for the patient. For example, IMD 14 may deliver electrical stimulation therapy to the patient via electrode 42A. In other examples, one or more additional or alternative electrodes 42 may be used to deliver the electrical stimulation therapy to the patient. In some examples, electrical sensing circuity 46 of IMD 14 may obtain a signal representative of an electrical response sensed from the patient in response to the electrical stimulation delivered to the patient according to the respective electrical stimulation parameter set or therapy program.

The electrical response obtained from the patient may be a measured voltage or a measured current from nerves and/or muscles and sensed by electrodes 42. In one example, electrode 42B senses a measured voltage response of a nerve fiber in response to the electrical stimulation delivered to the same nerve fiber according to the respective electrical stimulation parameter set. In another example, electrode 42B senses an electromyogram (EMG) signal of the patient. In another example, electrode 42B senses a nerve recording of an active potential of one or more nerves of the patient. In another example, electrode 42B senses a bioelectrical signal corresponding to an activity of a muscle fiber of the patient. In another example, electrode 42B senses a respective movement signal representative of a motion of a portion of the patient in response to the electrical stimulation. In this manner, one or more electrodes 42 may be configured to deliver electrical stimulation signals and/or sense evoked responses from tissue.

Electrical sensing circuitry 46 may receive respective sensed signals from one or more electrodes, such as electrode 42B, evoked from the electrical stimulation delivered according to the electrical stimulation parameter set. In some examples, electrical sensing circuitry 46 may perform signal processing of each received signal to remove noise or other unwanted frequencies. Electrical sensing circuitry 46 may also convert the analog signal to a digital signal and/or provide other signal processing functionality. Processing circuitry 32 may operate in conjunction with electrical sensing circuitry 46 to evaluate or analyze the received signal for voltage amplitudes, current amplitudes, frequency, and/or timing from the delivered stimulus. Using one or more of these characteristics of the sensed signal, processing 32 may determine whether or not the respective parameter set defined effective stimulation or if a different parameter set may be more effective. Once processor 32 determines that a parameter set defined stimulation that evoked a desired response from the patient, processor 32 may set that parameter set as the primary electrical stimulation parameter set and store the parameter set in memory for use in delivering subsequent therapy for the patient.

Additionally, or alternatively, electrical sensing circuitry 46 may be configured to determine a pressure or a volume of a bladder, a physical activity, a time of day, an amount of fluid intake, and/or an amount of caffeine consumed by the patient. As one example, electrical sensing circuitry may receive respective sensed signals from one or more electrodes 42, which may be analyzed by processing circuitry 32 to determine the pressure or the volume of the bladder of the patient. In turn, the pressure and/or the volume of the bladder may be used to determine a probability to experience a bladder related event function for the patient.

The architecture of IMD 14 illustrated in FIG. 2 is shown for exemplary purposes only. The techniques as set forth in this disclosure may be implemented in the example IMD 14 of FIG. 2, as well as other types of IMDs not described specifically herein. For example, processing circuitry 32 may be located within IMD 14, or within an external programming device used to configure or control IMD 14 remotely. Further, electrical sensing circuity 46 may be located within IMD 14, and/or within an external programming device that senses nerve response to electrical stimulation via one or more external electrodes or senses another physiological event of the patient (e.g., a pressure or a volume of a bladder, a physical activity, a time of day, an amount of fluid intake, and/or an amount of caffeine consumed by the patient). In other examples, IMD 14 may include or be in direct communication with other sensors, such as one or more accelerometers, pressure sensors, flow sensors, wetness sensors, or any other sensors that may provide information indicative of bladder related events of patient 12.

Figure 3:
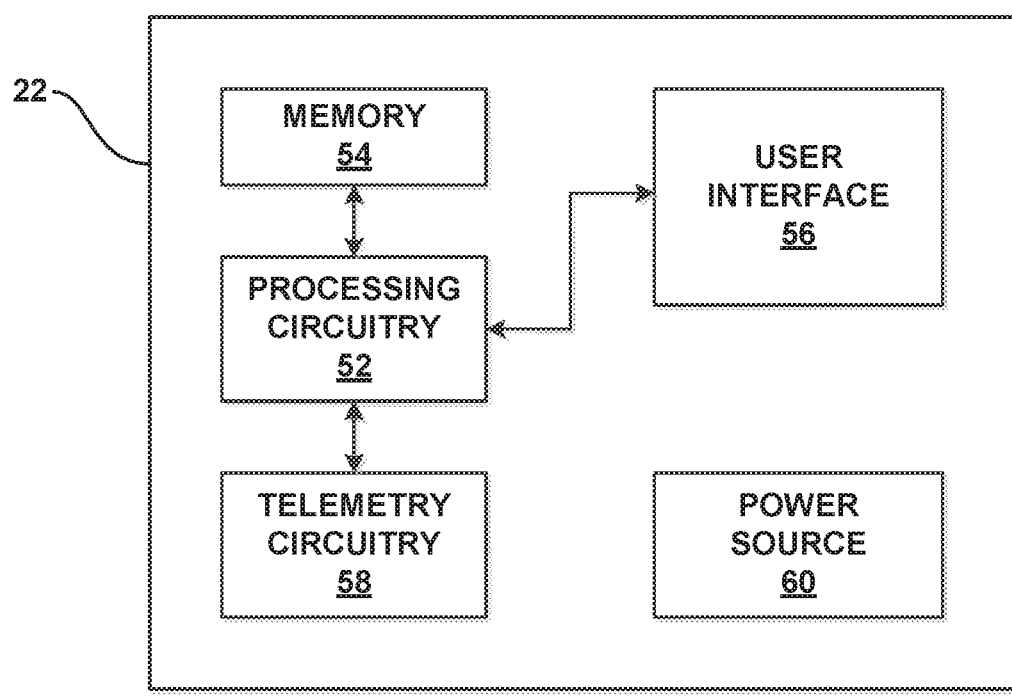
FIG. 3 is a block diagram illustrating an example external programmer.

FIG. 3 is a block diagram illustrating an example patient programmer 22. While patient programmer 22 may generally be described herein as a hand-held computing device, in other examples, patient programmer 22 may be a notebook computer, a cell phone, or a workstation, for example. As illustrated in FIG. 3, patient programmer 22 may include a processing circuitry 52, memory 54, telemetry circuitry 58, user interface 56, and power source 60. Memory 54 may store program instructions that, when executed by processing circuitry 52, cause processing circuitry 52 and patient programmer 22 to provide the functionality ascribed to patient programmer 22 throughout this disclosure.

In some examples, memory 54 may further include program information, e.g., stimulation programs similar to those stored in memory 34 of IMD 14. In some examples, the stimulation programs stored in memory 54 may be downloaded into memory 34 of IMD 14. Memory 54 may include any volatile, non-volatile, fixed, removable, magnetic, optical, or electrical media, such as RAM, ROM, CD-ROM, hard disk, removable magnetic disk, memory cards or sticks, NVRAM, EEPROM, flash memory, and the like. Processing circuitry 52 can take the form one or more microprocessors, DSPs, ASICs, FPGAs, programmable logic circuitry, or the like, and the functions attributed to processing circuitry 52 herein may be embodied as hardware, firmware, software or any combination thereof.

User interface 56 is configured to receive input from a user and may include, for example, a button or keypad, lights, a speaker for voice commands, a display, such as a LCD, LED, or CRT. In some examples, the display may include a touch sensitive screen. In some examples, processing circuitry 52 may receive patient input, e.g., patient input indicating a bladder related event, via user interface 56. The input may be, for example, in the form of pressing a button on a keypad or selecting an icon from a touch screen. In response to receiving the input, processing circuitry 52 may, for example, control telemetry circuitry 58 to deliver a signal that indicates receipt of the input to IMD 14, clinician programmer 20, or another device. This signal may, for example, be used to determine a probability to experience a bladder related event function for the patient, control delivery of therapy to the patient, and/or deliver therapy to the patient.

Processing circuitry 52 may also be configured to present information, e.g., information related to one or more sessions of electrical stimulation, electrical stimulation parameters, schedules of delivery of electrical stimulation, initiation of a particular stimulation session, and the like, to patient 12 or another user (e.g., a patient caretaker) via user interface 56. Although not shown, patient programmer 22 may additionally or alternatively include a data or network interface to another computing device, to facilitate communication with another device, e.g., IMD 14, and presentation of information relating to electrical stimulation via the other device.

Telemetry circuitry 58 supports wireless communication between IMD 14 and patient programmer 22 under the control of processing circuitry 52. Telemetry circuitry 58 may also be configured to communicate with another computing device, such as clinician programmer 20, via wireless communication techniques, or direct communication through a wired connection. Telemetry circuitry 58 may be substantially similar to telemetry circuitry 36 described above, providing wireless communication via an RF or proximal inductive medium. In some examples, telemetry circuitry 58 may include an antenna, which may take on a variety of forms, such as an internal or external antenna. An external antenna that is coupled to patient programmer 22 may correspond to a programming head that may be placed over IMD 14.

Examples of local wireless communication techniques that may be employed to facilitate communication between patient programmer 22 and another computing device include RF communication according to the 802.11 or Bluetooth® specification sets, infrared communication, e.g., according to the IrDA standard, or other standard or proprietary telemetry protocols. In this manner, other external devices may be capable of communicating with patient programmer 22 without needing to establish a secure wireless connection.

IMD 14, patient programmer 22, and/or clinician programmer 20 may control the delivery of electrical stimulation according to one or more stimulation programs based on input indicating a bladder related event, determination of a probability to experience a bladder related event function for the patient, and/or prediction of a timing of a future bladder related event. In some examples in which patient programmer 22 controls the stimulation, patient programmer 22 may transmit stimulation programs (e.g., the actual parameter values or an indication of the stimulation program) for implementation by IMD 14 to IMD 14 via telemetry circuitry 58. In some examples, a user (e.g., patient 12 or a clinician) may select one or more stimulation programs from a list provided via a display of user interface 56. Alternatively, patient programmer 22 may transmit a signal to IMD 14 indicating that IMD 14 should execute locally stored programs or therapy schedules. In such a manner, control over the electrical stimulation may be distributed between IMD 14 and patient programmer 22, or may reside in either one alone.

Power source 60 is configured to deliver operating power to the components of patient programmer 22. Power source 60 may include a battery and a power generation circuit to produce the operating power. In some examples, the battery may be rechargeable to allow extended operation. Recharging may be accomplished by electrically coupling power source 60 to a cradle or plug that is connected to an alternating current (AC) outlet. Additionally, or alternatively, recharging may be accomplished through proximal inductive interaction between an external charger and an inductive charging coil within patient programmer 22. In other examples, traditional batteries (e.g., nickel cadmium or lithium ion batteries) may be used. In addition, patient programmer 22 may be directly coupled to an alternating current outlet to power patient programmer 22. Power source 60 may include circuitry to monitor power remaining within a battery. In this manner, user interface 56 may provide a current battery level indicator or low battery level indicator when the battery needs to be replaced or recharged. In some cases, power source 60 may be capable of estimating the remaining time of operation using the current battery.

In some examples, clinician programmer 20 includes components similar to those of patient programmer 22 shown in FIG. 3. However, other configurations of clinician programmer 20 are contemplated.

As described above, the bladder related events described herein may include any number of events relating to bladder function of patient 12. For example, a bladder related event may include a void event and/or one or more symptoms relating to a bladder function event, such as, for example, leakage of urine, a sensation of pain or a similar perception in the pelvic and/or abdominal areas, a sensation of urge, urgency, suddenly needing to void or rapidly seeking a location to void, or combinations thereof. Although the probability to experience a bladder related event function will primarily be described with respect to probability to void functions below, the probability to void functions described below may additionally or alternatively include one or more other bladder related events.

Figure 4A:
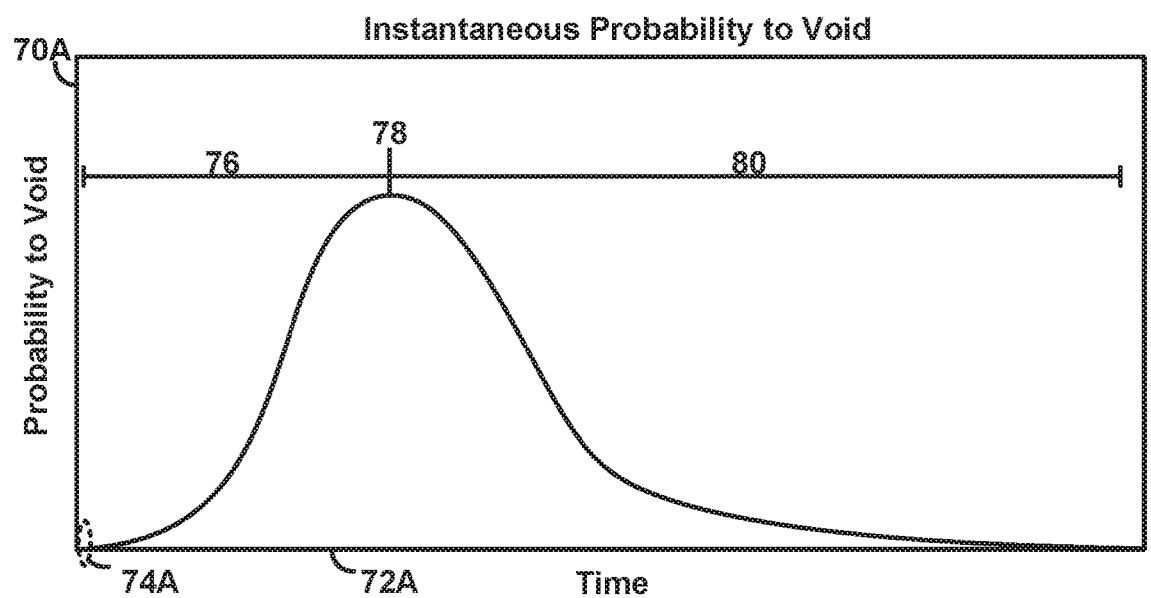
FIGS. 4A and 4B are graphs illustrating example probability to void functions for a patient.
Figure 4B:
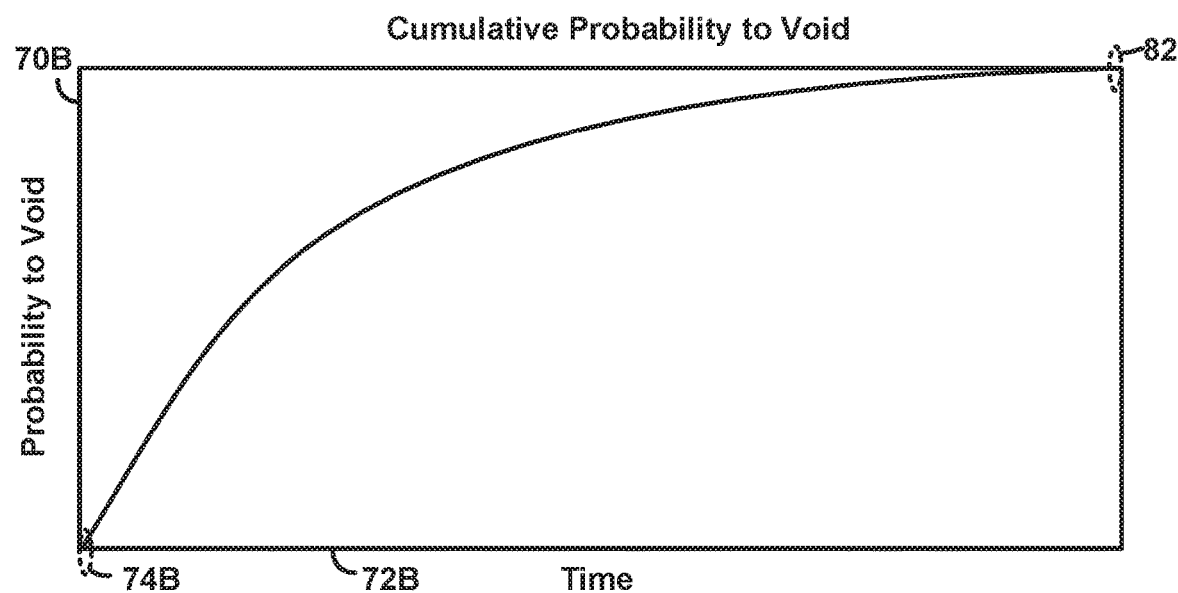

FIGS. 4A and 4B are graphs illustrating example probability to void functions for a patient. FIG. 4A is a graph illustrating an example instantaneous probability to void function for a patient. As seen in FIG. 4A, the instantaneous probability to void function includes a probability to void 70A as a function of time 72A. The probability to void 70A may be a probability that the patient will void a bladder at an elapsed time after a previous voiding event. The previous voiding event may be indicated by time zero 74A of the instantaneous probability to void function. For example, time zero 74A may the start of time after a previous voiding event, such a previous void event input by the patient via patient programmer 22.

The instantaneous probability to void function of FIG. 4A may take into account the probability of whether the patient has experienced a subsequent voiding event since the previous voiding event. For example, the instantaneous probability to void function of FIG. 4A increases 76 from time zero 74A until the probability to void 70A reaches a peak 78, and then decreases 80 after the peak 78. The decrease 80 after the peak 78 may indicate that it is likely the patient has already had a subsequent voiding event after the previous voiding event, which is why the probability to void decreases. In other words, the probability to void 70A begins to decrease 80 because if the patient has already had a first subsequent voiding event after the previous voiding event, it is less likely that the patient will have a second subsequent voiding event after the first subsequent voiding event.

The probability to void 70A of the instantaneous probability to void function may be a percentage, fraction, an integer indicating a probability that the patient will void the bladder at an elapsed time after a previous voiding event. In some examples, the peak 78 of the probability to void function may correspond to a probability to void of less than 100% (e.g., or less than 1). For example, the peak 78 may correspond to a probability to void of less than about 80%, about 60%, or about 50%. In other examples, the peak 78 may correspond to a different probability to void.

FIG. 4B is a graph illustrating an example cumulative probability to void function for a patient. Similar to the instantaneous probability to void function of FIG. 4A, the cumulative probability to void function includes a probability to void 70B as a function of time 72B. The probability to void 70B may be a probability that the patient will void a bladder at an elapsed time after a previous voiding event, where the previous voiding event may be indicated by time zero 74B of the cumulative probability to void function. For example, time zero 74B may the start of time after a previous voiding event, such a previous void event input by the patient via patient programmer 22.

Unlike the instantaneous probability to void function of FIG. 4A, however, the cumulative probability to void function may indicate the total probability that the patient has experienced a subsequent voiding event at any given time from the prior voiding event. For example, the cumulative probability to void function of FIG. 4B increases continuously from time zero 74B to an upper limit 82. If the cumulative probability to void function reaches upper limit 82, the cumulative probability to void function may begin to plateau at the value of the upper limit 82. Since the cumulative probability to void function represents to total probability that the patient has voided since the previous voiding event, the upper limit 82 may correspond to a probability of about 100% (e.g., or about 1) or close to about 100%. In other words, the upper limit may correspond to a probability of about 100% to indicate that the patient is likely to have a subsequent voiding event at any time based on the amount of time elapsed since the previous voiding event.

The instantaneous or the cumulative probability to void functions of FIGS. 4A and 4B may be used to predict a timing of a future void event of the patient. For example, the probability to void 70A or 70B may be compared to a respective threshold probability to void value to predict the timing of the future void event. As one example, if the probability to void 70A or 70B is greater than or equal the respective threshold probability to void value, a future void event may be predicted to occur at a time 72A or 72B from a previous voiding event corresponding to such a probability to void 70A or 70B.

In some examples, therapy is delivered to the patient based on the predicted timing of the future void event. For example, therapy may be controlled, withheld, and/or delivered to the patient based on a time until the predicted timing of the future void event. In some examples, a set of parameters defining the therapy delivered to the patient may be based on the time until the predicted timing of the future voiding event. IMD 14, patient programmer 22, clinician programmer 20, or another device may determine the time until the predicted timing of the future void event. For example, processing circuitry may be configured to predict the timing of the future void event as a specific time in the future, as an amount of time from time zero 74A or 74B, by implementing a countdown timer from time zero 74A or 74B, or the like, until the time corresponding to the respective threshold probability. The processing circuitry may also determine an amount of time until the predicted future void event by determining an amount of time elapsed or remaining, a percentage of time elapsed or remaining, or the like until the respective threshold of the probability to void function that may be used to predict a future void event. In some examples, the amount of time until the predicted future void event may be based on a current time.

In some examples, a set of parameters defining the therapy delivered to the patient may be based on the amount of time until the predicted future void event. For example, the processing circuitry may determine a first amount of time until the future void event and deliver a first therapy defined by a first set of parameters to the patient based on the first amount of time until the future void event. After the first therapy is delivered, the processing circuitry may determine a second amount of time until the future void event and deliver a second therapy defined by a second set of parameters to the patient based on the second amount of time until the future void event. In this manner, the second therapy may be a higher stimulation amplitude or use different electrodes from the first therapy to promote urine retention as compared to the first therapy. In some examples, the first and second amount of times until the future void event may correlate to percentages of time until the future void event. For example, the first therapy may be delivered based on a first amount of time corresponding to 25% of the timing of the predicted future void event, and the second therapy may be delivered based on a first amount of time corresponding to 50% of the timing of the predicted future void event. In other examples, other percentages or other amounts of time other than a percentage of time until the future void event may be used to deliver first and second therapies to the patient. Moreover, in some examples, three or more periods of time may be tracked between consecutive bladder related events and used to determine when to deliver therapy or what type of therapy to deliver during the respective time periods.

As another example, the processing circuitry may determine a first amount of time until the future void event and withhold a therapy based on the first amount of time until the future void event. For example, a first amount of time until the future void event may be compared to threshold value and the therapy may be withheld based on the comparison. In some such examples, it may be desirable to withhold therapy at certain amount of times from the predicted void event, such as if the probability to void is relatively low (e.g., the patient is unlikely to have a voiding event) at the first amount of time until the future void event. However, the system may begin delivering therapy once the time approaches closer to the predicted future voiding event in an attempt to prevent involuntary voiding. In some examples, the processing circuitry may determine a second amount of time until the future void event and deliver the therapy to the patient based on the second amount of time until the future void event. In some cases, the second amount of time until the predicted future void event may be less than the first amount of time until the predicted future void event. In other words, the second amount of time until the predicted future void event may occur further in time from the previous voiding event than the first amount of time until the predicted future void event.

In some examples, the system described herein may use one or more probability to void functions to determine the probability to void function for the patient, adapt the probability to void function for the patient, modify one or more parameters of a therapy, determine an efficacy of the therapy delivered to the patient, diagnose a urinary disorder of the patient, or combinations thereof. Although both instantaneous probability to void functions and cumulative probability to void functions are described as examples, a system may only need to use one of these types of functions to predict future voiding events.

Figure 5A:
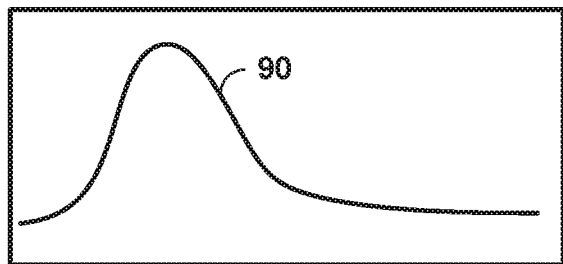
FIGS. 5A, 5B, 5C, 5D, 5E, and 5F are graphs illustrating example instantaneous probability to void functions.

FIGS. 5A-5F are graphs illustrating example instantaneous probability to void functions, with the probability to void being shown on the y-axis and time on the x-axis. FIG. 5A is a graph illustrating an example instantaneous probability to void function of a "normal" instantaneous probability to void function 90. The normal instantaneous probability to void function 90 of FIG. 5A may be an instantaneous probability to void function of a patient or a plurality of subjects that have normal bladder function (e.g., do not experience bladder dysfunction).

For ease of description, the graphs of FIGS. 5B-5F will be described with respect to the normal instantaneous probability to void function 90. In other examples, however, one or more different instantaneous probability to void functions may be used to determine the probability to void function for the patient, adapt the probability to void function for the patient, modify one or more parameters of a therapy, determine an efficacy of the therapy delivered to the patient, detect a urinary condition of the patient, or combinations thereof. For example, an instantaneous probability to void function of a patient with an overactive bladder or an instantaneous probability to void function based on a plurality of subjects with overactive bladders may be used to determine the probability to void function for the patient, adapt the probability to void function for the patient, modify one or more parameters of a therapy, determine an efficacy of the therapy delivered to the patient, and/or detect a urinary condition of the patient. Moreover, although the instantaneous probability to void functions are described with respect to being for a single patient, in other examples, the instantaneous probability to void functions may be based on a plurality of subjects, an average, historical data, or the like (e.g., a composite probability to void function). The graphs of FIGS. 5A-5F may be similar to the instantaneous probability function of FIG. 4A, such that the graphs are plotted probability to void versus time.

Figure 5B:
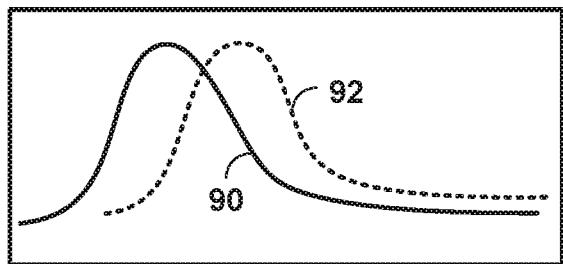

FIG. 5B is a graph illustrating an example normal instantaneous probability to void function 90 and an example instantaneous probability to void function 92 of a patient with urinary retention. In some examples, instantaneous probability to void function 92 is an instantaneous probability to void function of a patient with type-A urinary retention. As seen in FIG. 5B, urinary retention may be characterized by a shift to the right in comparison to the normal probability to void function 90. For example, the instantaneous probability to void function 92 for the patient with urinary retention, may indicate a longer amount of time before a predicted voiding event. In other words, the instantaneous probability to void function 92 may have probabilities to void comparable to the normal instantaneous probability to void function 90, but at times greater than that of the normal probability to void function 90.

Figure 5C:
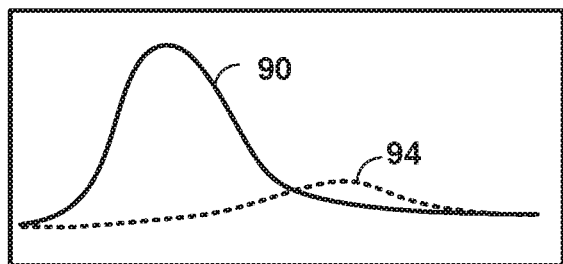

FIG. 5C is a graph illustrating an example normal instantaneous probability to void function 90 and another example instantaneous probability to void function 94 of a patient with urinary retention. In some examples, instantaneous probability to void function 94 is an instantaneous probability to void function of a patient with type-B urinary retention. As seen in FIG. 5C, the instantaneous probability to void function 94 of the patient with urinary retention may be shifted in time to the right, similar to instantaneous probability to void function 92 of FIG. 5B. For example, the peak of the instantaneous probability to void function 94 occurs at a later time that the peak of the normal instantaneous probability to void function.

In addition to the shift of the instantaneous probability to void function 94 in comparison to the normal probability to void function, the instantaneous probability to void function 94 of FIG. 5C also exhibits a decrease in the probabilities to void overall. For example, the amplitude of the peak of the instantaneous probability to void function 94 is significantly smaller than that of the normal instantaneous probability to void function 90. In other words, the instantaneous probability to void function 94 of the patient with type-B urinary retention may indicate a lower probability to void at some, most, or even all times in comparison to the normal instantaneous probability to void function 90.

Figure 5D:
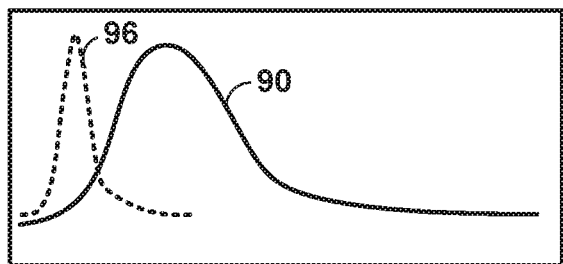

FIG. 5D is a graph illustrating an example normal instantaneous probability to void function 90 and an example instantaneous probability to void function 96 of a patient with an overactive bladder and/or urinary incontinence. As seen in FIG. 5D, an overactive bladder and/or urinary incontinence may be characterized by a shift to the left in comparison to the normal probability to void function 90. For example, the instantaneous probability to void function 96 for the patient with overactive bladder and/or urinary incontinence, may indicate a shorter amount of time before a predicted voiding event, a higher probability of a voiding event at shorter amounts of time, or both in comparison to normal instantaneous probability to void function 90. In other words, the instantaneous probability to void function 92 may have probabilities to void comparable to the normal instantaneous probability to void function 90, but at times less than that of the normal probability to void function 90. In addition, or as an alternative, the amplitude of the peak of the instantaneous probability to void function 96 may be larger than that of the normal instantaneous probability to void function 90.

Figure 5E:
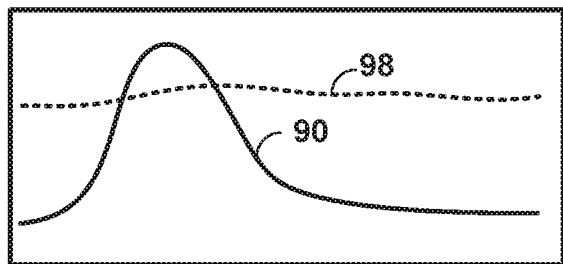

FIG. 5E is a graph illustrating an example normal instantaneous probability to void function 90 and another example instantaneous probability to void function 98 of a patient with overactive bladder and/or urinary incontinence. As seen in FIG. 5E, the instantaneous probability to void function 98 of a patient with overactive bladder and/or urinary incontinence may exhibit an increase in the probabilities to void. For example, the instantaneous probability to void function 96 of the patient with overactive bladder and/or urinary incontinence may indicate a higher probability to void at some, most, or even all times in comparison to the normal instantaneous probability to void function 90.

Figure 5F:
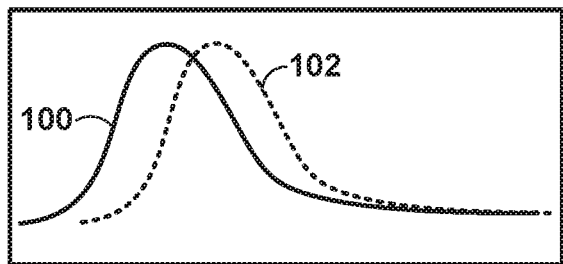

FIG. 5F is a graph illustrating an example instantaneous probability to void function 100 for a patient during the day and an example instantaneous probability to void function 102 for a patient at night (e.g., when the patient may be asleep). As seen in FIG. 5F, the instantaneous probability to void function 102 for the patient at night may be shifted to the right in comparison to the probability to void function 100 for the patient during the day. For example, the instantaneous probability to void function 102 for the patient at night, may indicate a longer amount of time before a predicted future void event. In other words, the instantaneous probability to void function 102 for the patient at night may have probabilities to void comparable to the instantaneous probability to void function 100 for the patient during the day, but at times greater than that of the probability to void function 100 for the patient during the day. According to the different probability to void functions shown in FIGS. 5B-5F, a system, such as system 10, may be configured to identify different bladder dysfunctions of patient 12 and/or changes to bladder functionality for patient 12. In some examples, system 10 may deliver therapy and/or modify therapy in response to identifying a particular probability to void function for patient 12.

Figure 6A:
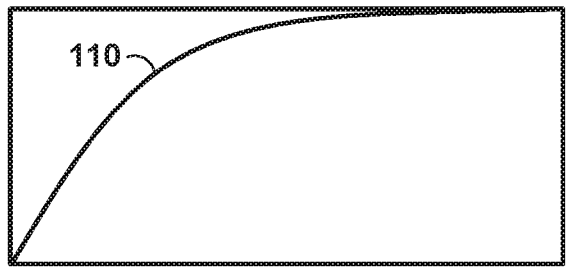
FIGS. 6A, 6B, 6C, 6D, and 6E are graphs illustrating example cumulative probability to void functions.

FIGS. 6A-6E are graphs illustrating example cumulative probability to void functions, with the probability to void being shown on the y-axis and time on the x-axis. FIG. 6A is a graph illustrating an example cumulative probability to void function of a "normal" cumulative probability to void function 110. The normal cumulative probability to void function 110 of FIG. 6A may be a cumulative probability to void function of a patient or a cumulative composite probability to void function of a plurality of subjects that have normal bladder function (e.g., do not experience bladder dysfunction).

For ease of description, the graphs of FIGS. 6B-6E will be described with respect to the normal cumulative probability to void function 110. In other examples, however, a system may utilize one or more different cumulative probability to void functions to determine the probability to void function for the patient, adapt the probability to void function for the patient, modify one or more parameters of a therapy, determine an efficacy of the therapy delivered to the patient, detect a urinary condition of the patient, or combinations thereof. For example, a cumulative probability to void function of a patient with an overactive bladder or a cumulative composite probability to void function based on a plurality of subjects with overactive bladders may be used to determine the probability to void function for the patient, modify the probability to void function for the patient, determine when to delivery therapy for the patient, modify one or more parameter values that define a therapy, determine an efficacy of the therapy delivered to the patient, and/or detect a urinary condition of the patient. Moreover, although the cumulative probability to void functions are described with respect to being for a single patient, in other examples, the cumulative probability to void functions may be a cumulative composite probability to void function based on a plurality of subjects, an average, historical data, or the like. The graphs of FIGS. 6A-6E may be similar to the cumulative probability function of FIG. 4B, such that the graphs are plotted with the probability to void versus time.

Figure 6B:
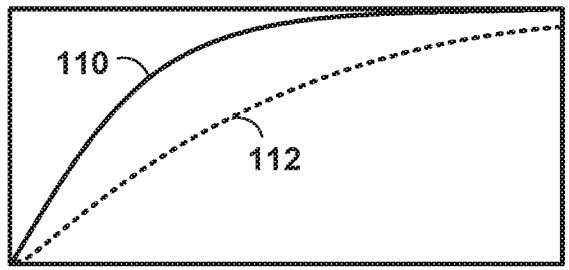

FIG. 6B is a graph illustrating an example normal cumulative probability to void function 110 and an example cumulative probability to void function 112 of a patient with urinary retention. As seen in FIG. 6B, urinary retention may be characterized by a reduced cumulative probability to void function and/or a shift of the probability to void curve to the right in comparison to the normal probability to void function 110. For example, the cumulative probability to void function 112 for the patient with urinary retention, may indicate a longer amount of time before a predicted voiding event, a longer amount of time before reaching an upper limit of the probability to void, or both. In some examples, the cumulative probability to void function 112 may have probabilities to void comparable to the normal cumulative probability to void function 110, but at times greater than that of the normal probability to void function 110. In other examples, the cumulative probability to void function 112 may also exhibit a decrease in the probabilities to void overall when compared to the normal probability to void function 110. In other words, the cumulative probability to void function 112 of the patient with urinary retention may indicate a lower probability to void at some, most, or even all times in comparison to the normal cumulative probability to void function 110.

Figure 6C:
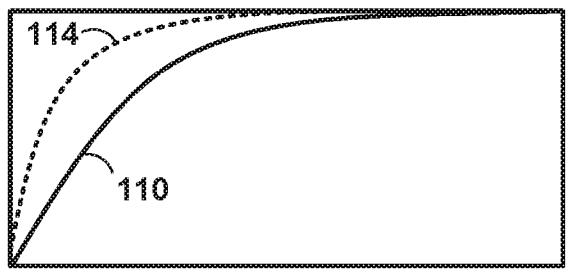

FIG. 6C is a graph illustrating an example normal cumulative probability to void function 110 and an example cumulative probability to void function 114 of a patient with an overactive bladder and/or urinary incontinence. As seen in FIG. 6C, an overactive bladder and/or urinary incontinence may be characterized by an increased cumulative probability to void function and/or a shift of the probability to void curve to the left in comparison to the normal cumulative probability to void function 110. For example, the cumulative probability to void function 112 for the patient with an overactive bladder and/or urinary incontinence, may indicate a shorter amount of time before a predicted voiding event, a higher probability of a voiding event at shorter amounts of time, or both in comparison to normal cumulative probability to void function 110. In other words, the cumulative probability to void function 112 may have probabilities to void comparable to the normal cumulative probability to void function 110, but at times less than that of the normal probability to void function 110. In addition, or as an alternative, the cumulative probability to void function 112 may reach an upper limit sooner than that of the normal cumulative probability to void function 110. Moreover, in some examples, the cumulative probability to void function 112 of the patient with an overactive bladder and/or urinary incontinence may indicate a higher probability to void at some, most, or even all times in comparison to the normal cumulative probability to void function 110.

Figure 6D:
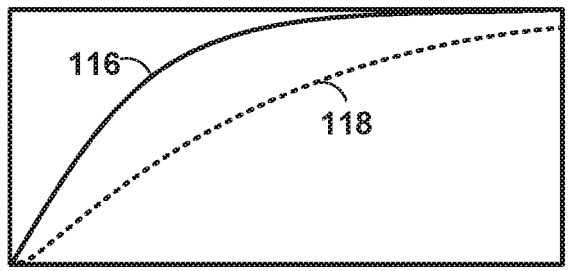

FIG. 6D is a graph illustrating an example cumulative probability to void function 116 for a patient during the day and an example cumulative probability to void function 118 for a patient at night (e.g., when the patient may be asleep). As seen in FIG. 6D, the cumulative probability to void function 118 for the patient at night may be reduced or shifted to the right in comparison to the probability to void function 116 for the patient during the day. For example, the cumulative probability to void function 118 for the patient at night, may indicate a longer amount of time before a predicted future void event. In other words, the cumulative probability to void function 118 for the patient at night may have probabilities to void comparable to the cumulative probability to void function 116 for the patient during the day, but at times greater than that of the probability to void function 116 for the patient during the day. In some examples, the cumulative probability to void function 118 for the patient at night may also exhibit a decrease in the probabilities to void overall in comparison to the probability to void function 116 for the patient during the day. In other words, the cumulative probability to void function 118 for the patient at night may indicate a lower probability to void at some, most, or even all times in comparison to the cumulative probability to void function 116 for the patient during the day. In this manner, if patient 12 has probabilities to void that are different for different periods of the day, such as daytime vs. nighttime (e.g., while patient 12 is sleeping), a system may change therapy delivery times and/or therapy parameter values for different time periods to accommodate these differences in predicted future voiding events.

Figure 6E:
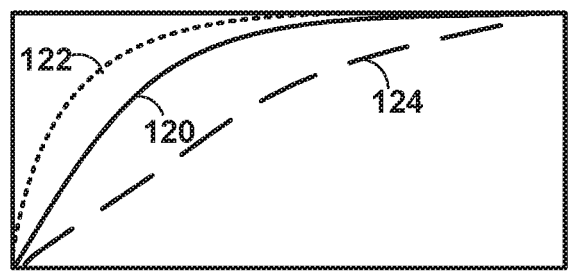

FIG. 6E is a graph illustrating an example cumulative probability to void function 120 for a patient with normal fluid intake amounts, an example cumulative probability to void function 122 for a patient with increased (e.g., in comparison to normal) fluid intake amounts, and an example cumulative probability to void function 124 for a patient with decreased (e.g., in comparison to normal) fluid intake amounts. As described above, in some examples, the system described herein may determine the probability to void function for the patient based on an amount of fluid intake by the patient. As seen in FIG. 6E, the cumulative probability to void function 120 for a patient with normal fluid intake amounts may be similar to the normal cumulative probability to void function 110 of FIGS. 6A-6D, the cumulative probability to void function 122 for a patient with increased fluid intake amounts may be similar to the cumulative probability to void function 114 of FIG. 6C, and the cumulative probability to void function 124 for a patient with decreased fluid intake amounts may be similar to the cumulative probability to void function 112 of FIG. 6B. For example, the cumulative probability to void function 122 for a patient with increased fluid intake amounts may be characterized by an increased cumulative probability to void function and/or a shift to the left in comparison to the cumulative probability to void function 120. As another example, the cumulative probability to void function 124 for a patient with decreased fluid intake amounts may be characterized by a reduced cumulative probability to void function and/or a shift to the right in comparison to the probability to void function 120. In this manner, a system may shift the probability to void function to the left or right based on determined fluid intake of the patient 12 and change therapy delivery according to the updated probability to void function determined based on fluid intake for the patient.

In some examples, comparisons similar to that of FIGS. 5B-5F and/or FIGS. 6B-6E may be used to determine the probability to void function for the patient, adapt the probability to void function for the patient, detect changes to bladder functionality and/or diagnose patient disorders, determine when to delivery therapy to the patient, modify one or more parameters of a therapy, determine an efficacy of the therapy delivered to the patient, detect a urinary condition of the patient, or combinations thereof. As one example, a probability to void function for the patient may be selected based on an age, a gender, and/or a body composition of the patient. In another example, a composite probability to void function based on plurality of subjects may be selected based on the age, gender, and/or body composition of the patient such that at least some of the plurality of subjects have an age, gender, and/or body composition similar to that of the patient (e.g., within a predetermined range of the patient). The composite probability to void function based on the plurality of subjects may then be adjusted based on the timing of the plurality of bladder voiding events of the patient. For example, if the timing of the bladder voiding events of the patient indicate a shorter amount of time before a predicted voiding event, a higher probability of a voiding event at shorter amounts of time, or the like in comparison to the probability to void function based on the plurality of subjects, the probability to void function based on the plurality of subjects may be shifted to the left to determine the probability to void function for the patient.

A system may adjust or modify, based on one or more probability to void functions, one or more therapy parameters that at least partially define the therapy delivered to the patient. For example, the system described herein may be configured to continue identifying a timing a plurality of subsequent voiding events after delivering therapy based on a predicted future voiding event. The system may then update or modify the probability to void function for the patient based on the continually identified timing of the plurality of subsequent bladder voiding events. As one example, the probability to void function may be adapted based on subsequently identified voiding events by shifting the probability to void function to the right, such as in the case in which the therapy resulted in reduced overactivity and/or urinary incontinence of the patient. The system may then predict a timing of a subsequent future void event based on the adapted probability to void function for the patient and, in some examples, may modify at least one parameter of the therapy based on the adapted probability to void function for the patient. For example, the system may wait longer from the last void event before delivering therapy because the patient can autonomously retain urine for a longer period of time. In another example, the system may reduce the voltage or current amplitude, or reduce the pulse width, that at least partially defines the therapy based on the adapted probability to void function for the patient. The modified therapy can be delivered to the patient based on the predicted timing of the subsequent future void event.

As another example, the system described herein may be configured to continue identifying a timing a plurality of subsequent voiding events after delivering therapy based on a predicted future voiding event, and the system may determine a second probability to void function for the patient based on the timing of the plurality of subsequent bladder voiding events. The system may use the second probability to void function to determine the efficacy of the previously delivered therapy. For example, the first probability to void function may be compared to the second probability to void function for the patient. If the second probability to void function is a function more similar to a "normal" probability to void function in comparison to the first probability to void function for the patient, the system may determine that the second probability to void function indicates that the therapy is efficacious and improving the patient's system related to bladder dysfunction. If the second probability to void function is a function less similar to a "normal" probability to void function in comparison to the first probability to void function for the patient or if the second probability to void function is not different than the first probability to void function, the system may determine that the second probability to void function indicates that the previously delivered therapy is not efficacious, or at least is not as effective as desired to reduce patient symptoms. In turn, the system may be able to modify one or more parameters of the therapy in order to provide efficacious therapy to the patient.

In other example, the system may compare the second probability to void function to the previously determined first probability to void function to determine if the patient's bladder function has improved, stayed the same, or declined over time. If the second probability to void function represents a shift of the curve to the right, indicating longer times between voiding events, the system may determine that the therapy is effective and/or the patient's condition is improving. If the second probability to void function represents a shift of the curve to the left, indicating shorter times between voiding events, the system may determine that the therapy is ineffective and/or the patient's condition is worsening. The system may thus change, or prompt the patient or physician to change, timing of therapy delivery or modify therapy parameters in an attempt to reduce patient symptoms. In addition, or alternatively, the system may evaluate the changes to the shape of the curve between different probability to void functions in order to identify how the symptoms are changing and/or which therapy parameter values need to be adjusted.

Additionally, or alternatively, the second probability to void function for the patient may be compared to a composite probability to void function based on plurality of subjects to determine the efficacy of the therapy. For example, if the second probability to void function determined for the patient is a function similar to a "normal" composite probability to void function based on a plurality of subjects, the second probability to void function for the patient may indicate that the therapy is efficacious. If the second probability to void function is a function not similar to a "normal" composite probability to void function, or if the second probability to void function is similar to a probability to void function based on a plurality of subjects with urinary retention, overactive bladders, urinary incontinence, or another bladder dysfunction, the system may determine that the second probability to void function indicates that the therapy is not efficacious. In turn, the system may be able to change the timing of therapy and/or adjust one or more therapy parameter values defining the therapy in order to improve efficacy of the therapy delivered to the patient.

The system may also be able to detect a urinary condition of the patient based on the determined probability to void function for the patient. For example, the probability to void function for the patient may be compared to a plurality of subjects with urinary retention to determine if the patient exhibits urinary retention, compared to a plurality of subjects with overactive bladders to determine if the patient has an overactive bladder, compared to a plurality of subjects with urinary incontinence to determine if the patient exhibits urinary incontinence, or the like. If it is determined that the probability to void function for the patient is similar to any of the probability to void functions based on the plurality of subjects exhibiting a certain condition or urinary disorder, the system may be able to determine that the patient also exhibits such a condition or urinary disorder. In some examples, the detection of a urinary condition of the patient may be performed in order to determine if the patient is a candidate to receive an 1 MB, would benefit from therapy to reduce symptoms of bladder dysfunction, or the like. In this way, in some cases, the detection of the urinary condition may be determined prior to implantation of 1 MB 14 (FIG. 1) or another device configured to deliver therapy to the patient.

In some examples, such comparisons may enable the system described herein to learn which parameters of the therapy are the most efficacious to the patient, modify or adapt the therapy delivered to the patient as needed, detect a condition of the patient, or the like to better fit the needs of the particular patient. In addition, the system described herein may be configured to modify or adjust the probability to void function for the patient, one or more parameters of the therapy delivered to the patient, or the like such that the therapy delivered and the information obtained by the system can be updated on an ongoing basis. In this way, changes in patient condition, efficacy of the therapy, or the like can be determined and addressed using the system described herein.

Figure 7A:
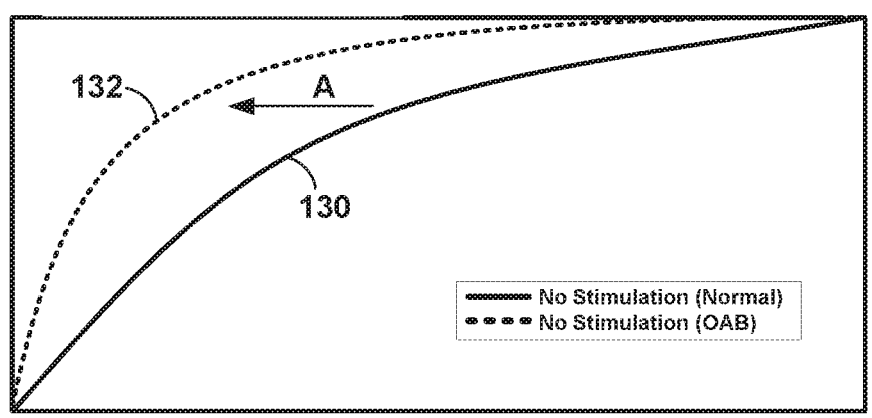
FIG. 7A is a graph illustrating example cumulative probability to void functions for a patient with a normal bladder and for a patient with an overactive bladder.

FIG. 7A is a graph illustrating example cumulative probability to void functions for a patient with a normal bladder and for a patient with an overactive bladder. As seen in FIG. 7A, the cumulative probability to void function 130 for a patient with normal bladder function, may be shifted in the direction of arrow A in the case of a patient with overactive bladder or increasing symptoms of overactive bladder to be similar to the cumulative probability to void function 132. In the example, of FIG. 7A, neither of the cumulative probability to void functions 130 or 132 were based on patients who received delivered therapy, such as by IMD 14 (FIG. 1). In this manner, recognition that the curve of the probability to void function 132 is shifted left of the normal probability to void function 130 indicates that the patient is experiencing decreased time between voiding events and potentially suffering from overactive bladder.

Figure 7B:
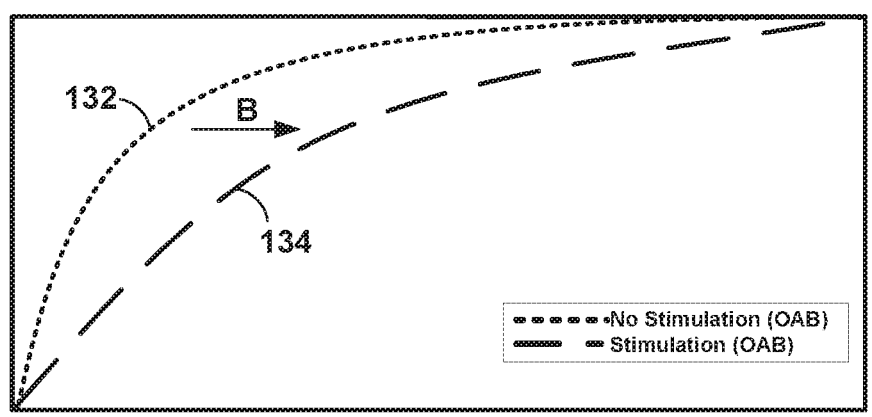
FIG. 7B is a graph illustrating example cumulative probability to void functions for a patient with an overactive bladder without stimulation therapy and receiving therapy.

FIG. 7B is a graph illustrating example cumulative probability to void functions for a patient with an overactive bladder that indicate changes due to delivered therapy. As seen in the example of FIG. 7B, the cumulative probability to void function 132 for a patient indicates an overactive bladder. However, after receiving therapy, the curve of the cumulative probability to void function 132 may be shifted in the direction of arrow B, or to the right, after the patient receives therapy to result in cumulative probability function 134. In the example of FIG. 7B, the cumulative probability to void function 134 for the patient receiving the therapy may indicate that the patient is receiving efficacious therapy because the cumulative probability to void function 134 has shifted to the right of the previously determined probability to void function 132 indicating bladder dysfunction. In some examples, cumulative probability to void function 134 may be compared to the normal cumulative probability function 130 of FIG. 7A in order to determine how effective the therapy is at reducing symptoms related to overactive bladder.

Figure 8A:
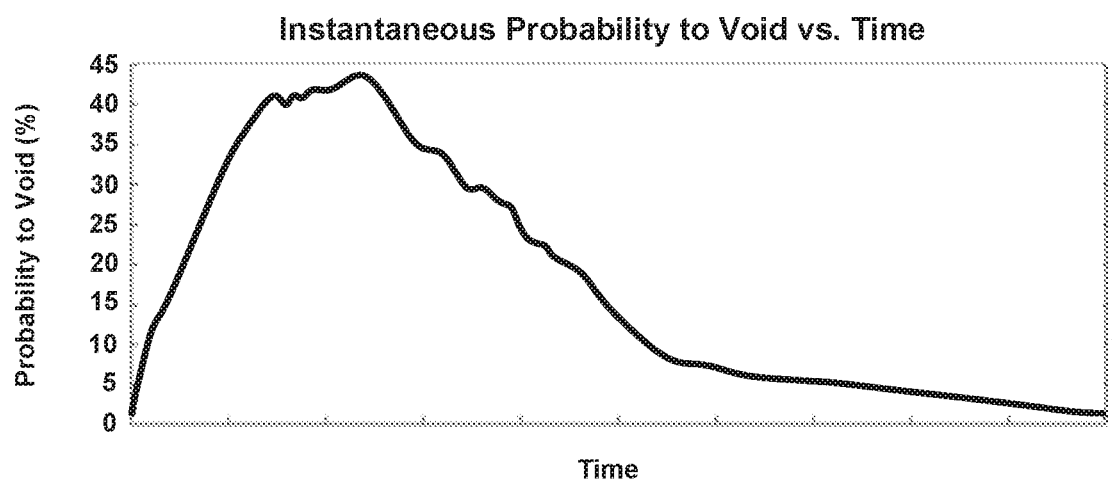
FIG. 8A is a graph illustrating an example instantaneous probability to void function for a patient in terms of probability to void as a function of time.
Figure 8B:
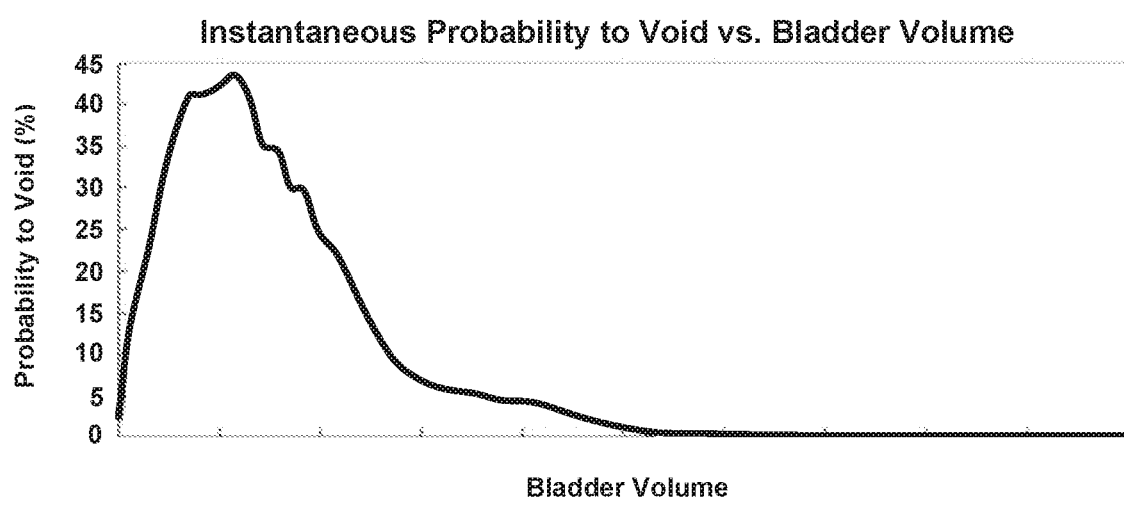
FIG. 8B is a graph illustrating an example instantaneous probability to void function for a patient in terms of probability to void as a function of bladder volume.

FIG. 8A is a graph illustrating an example instantaneous probability to void function for a patient in terms of probability to void as a function of time. FIG. 8B is a graph illustrating an example instantaneous probability to void function for a patient in terms of probability to void as a function of bladder volume. As described above, the probability to void function for a patient can be determined based on at least one of a pressure of the bladder of the patient, a volume of the bladder of the patient, a physical activity of the patient, a time of day, an amount of fluid intake of the patient, or an amount of caffeine consumed by the patient. As seen in FIGS. 8A and 8B, the instantaneous probability to void function based on the volume of the bladder of the patient may be similar to the instantaneous probability to void function based on time. In some examples, the instantaneous probability to void function of FIG. 8B may be used to determine the instantaneous probability to void function for the patient of FIG. 8A. For example, an instantaneous probability to void function based on a plurality of subjects may be adjusted based on the instantaneous probability to void function of FIG. 8B that incorporates information relating to the volume of the bladder of the patient. In addition, the curves of FIGS. 8A and 8B are relatively similar, indicating that time can be used as a proxy for detecting a physiological indicator of bladder filling such as bladder volume. Therefore, a probability to void based on time can be an effective measure to predict subsequent voiding events.

Figure 9A:
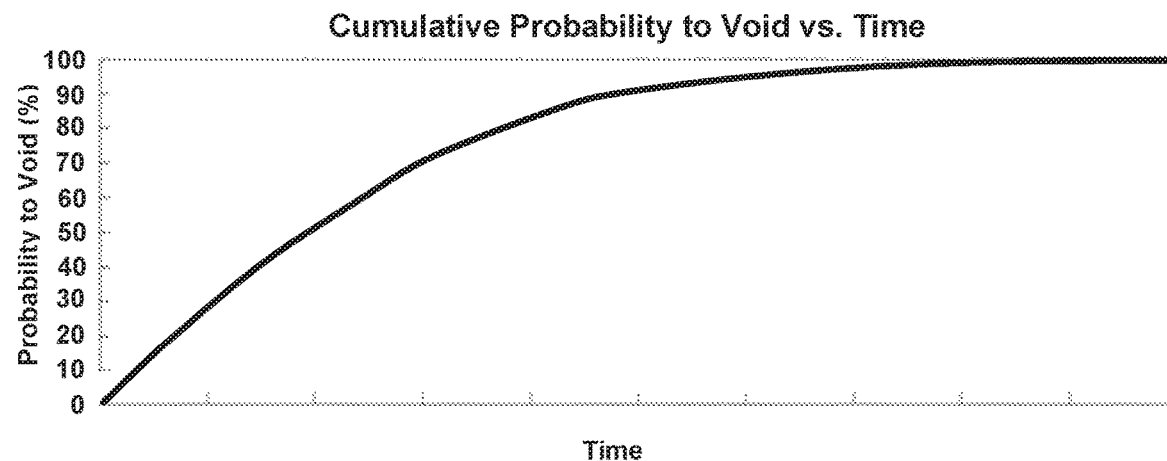
FIG. 9A is a graph illustrating an example cumulative probability to void function for a patient in terms of probability to void as a function of time.
Figure 9B:
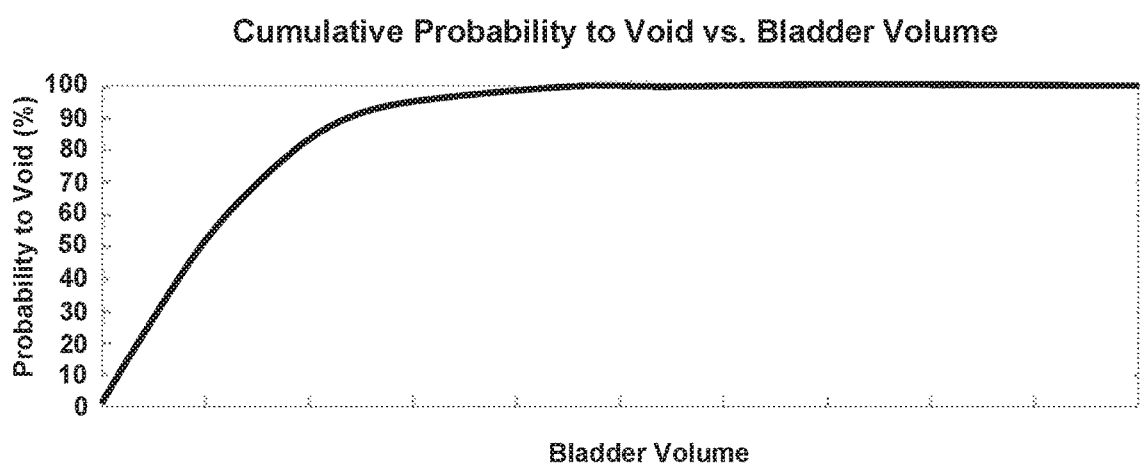
FIG. 9B is a graph illustrating an example cumulative probability to void function for a patient in terms of probability to void as a function of bladder volume.

FIG. 9A is a graph illustrating an example cumulative probability to void function for a patient in terms of probability to void as a function of time. FIG. 9B is a graph illustrating an example cumulative probability to void function for a patient in terms of probability to void as a function of bladder volume. As seen in FIGS. 9A and 9B, the cumulative probability to void function based on the volume of the bladder of the patient may be similar to the cumulative probability to void function based on time. Similar to FIGS. 8A and 8B, in some examples, the cumulative probability to void function of FIG. 9B may be used to determine the cumulative probability to void function for the patient of FIG. 9A.

In some examples, the efficacy of therapy delivered to the patient may be determined based on at least one of a pressure of the bladder of the patient, a volume of the bladder of the patient, a physical activity of the patient, a time of day, an amount of fluid intake of the patient, or an amount of caffeine consumed by the patient. However, as shown by the similarity between the curves of FIGS. 9A and 9B, time may be used as a proxy for a physiologically detected parameter such as bladder volume to predict when a subsequent voiding event may occur.

Figure 10A:
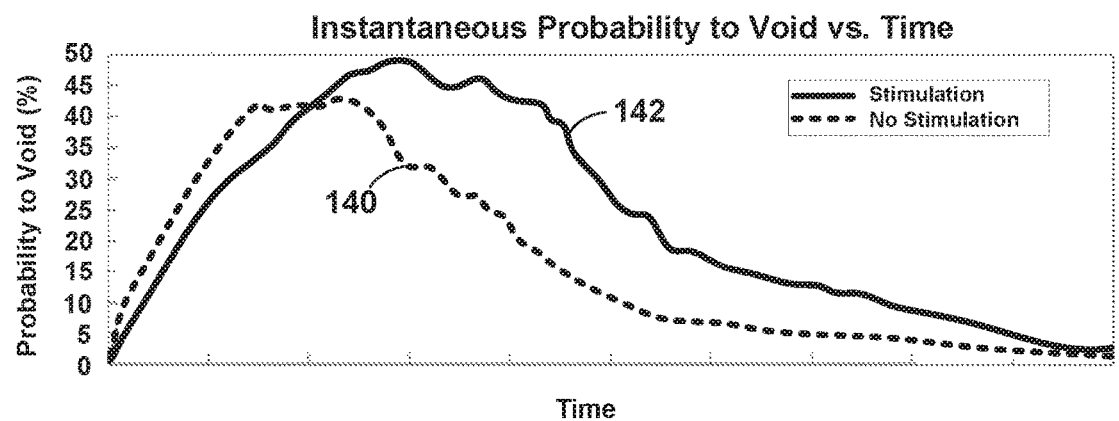
FIG. 10A is a graph illustrating example instantaneous probability to void functions for a patient not receiving therapy and receiving therapy in terms of probability to void as a function of time.
Figure 10B:
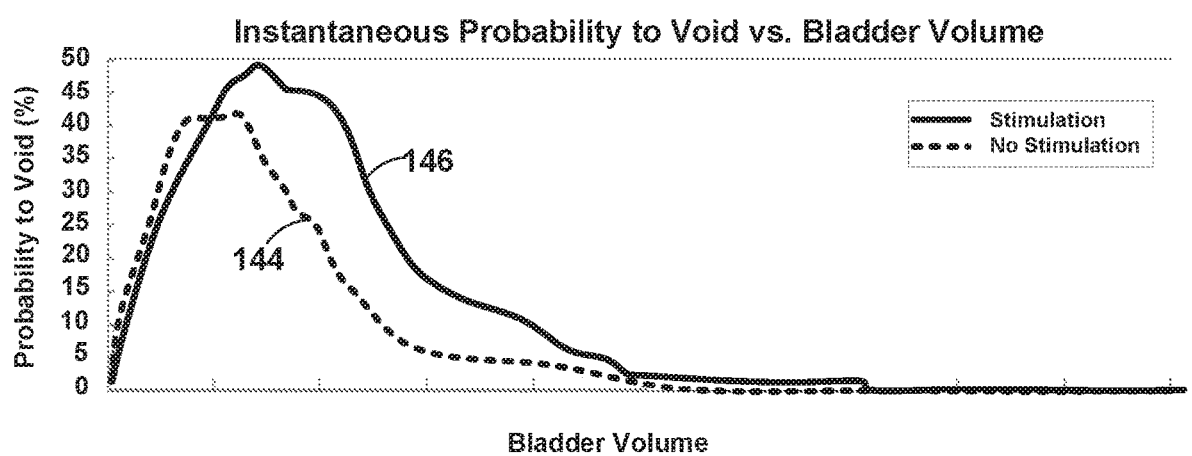
FIG. 10B is a graph illustrating example instantaneous probability to void functions for a patient not receiving therapy and receiving therapy in terms of probability to void as a function of bladder volume.

FIG. 10A is a graph illustrating example instantaneous probability to void functions for a patient not receiving therapy (instantaneous probability to void function 140) and for a patient receiving therapy (instantaneous probability to void function 142) in terms of probability to void as a function of time. FIG. 10B is a graph illustrating example instantaneous probability to void functions for a patient not receiving therapy (instantaneous probability to void function 144) and for a patient receiving therapy (instantaneous probability to void function 146) in terms of probability to void as a function of bladder volume. The instantaneous probability to void functions of FIGS. 10A and 10B may be for the same patient, and the patient may suffer from overactive bladder. As seen in FIGS. 10A and 10B, both graphs may indicate that the patient is receiving efficacious therapy. For example, both the graph of FIG. 10A and the graph of FIG. 10B show that the electrical stimulation therapy resulted in instantaneous probability to void functions 142 and 146 that are shifted to the right of the instantaneous probability to void functions 140 and 144, respectively, of the patient prior to therapy. In some examples, similar information may be determined using cumulative probability to void functions. A system may continually monitor changes to the instantaneous probability to void function over time to determine if changes to therapy should be made based on whether or not the instantaneous probability to void function moves to the left or right.

Figure 11A:
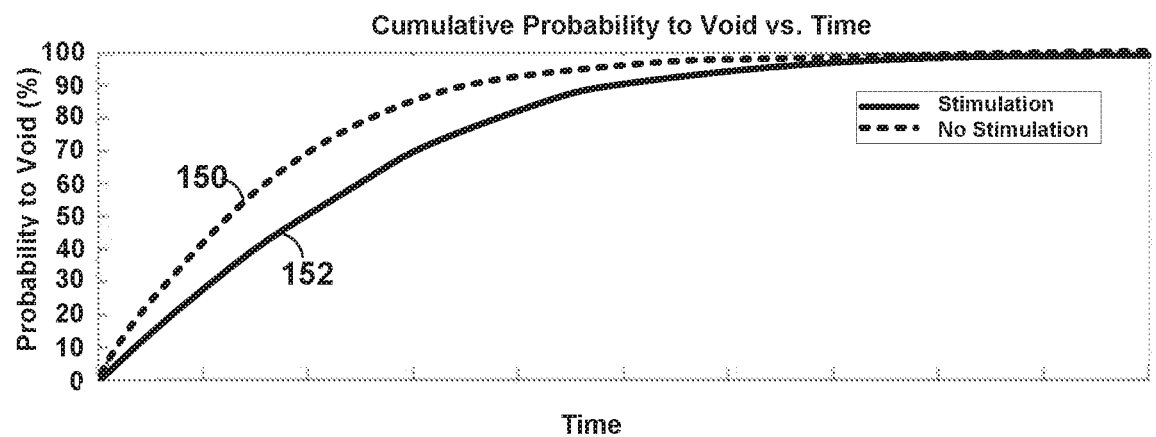
FIG. 11A is a graph illustrating example cumulative probability to void functions for a patient not receiving therapy and receiving therapy in terms of probability to void as a function of time.
Figure 11B:
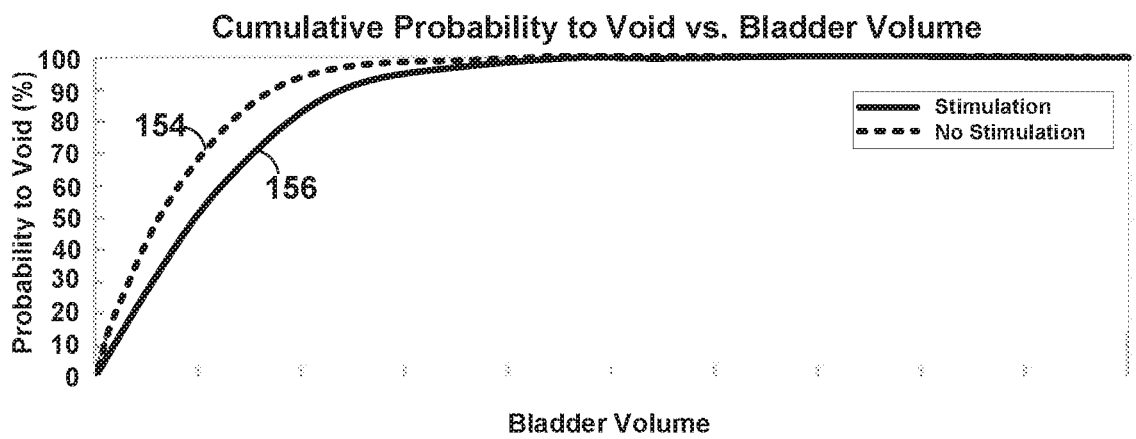
FIG. 11B is a graph illustrating example cumulative probability to void functions for a patient not receiving therapy and receiving therapy in terms of probability to void as a function of bladder volume.

FIG. 11A is a graph illustrating example cumulative probability to void functions for a patient not receiving therapy (instantaneous probability to void function 150) and for a patient receiving therapy (instantaneous probability to void function 152) in terms of probability to void as a function of time. FIG. 11B is a graph illustrating example cumulative probability to void functions for a patient not receiving therapy (instantaneous probability to void function 154) and for a patient receiving therapy (instantaneous probability to void function 156) in terms of probability to void as a function of bladder volume. The cumulative probability to void functions of FIGS. 11A and 11B may be for the same patient, and the patient may suffer from an overactive bladder. As seen in FIGS. 11A and 11B, both graphs may indicate that the patient is receiving efficacious therapy. For example, both the graph of FIG. 11A and the graph of FIG. 11B show that the electrical stimulation therapy resulted in cumulative probability to void functions 152 and 156 that are reduced and/or shifted to the right of the cumulative probability to void functions 150 and 154, respectively, of the patient prior to therapy. A system may continually monitor changes to the cumulative probability to void function over time to determine if changes to therapy should be made based on whether or not the cumulative probability to void function moves to the left or right.

As described herein, the system may monitor for changes to the probability to void function of a patient over time as an indicator of disease progression and/or therapy efficacy. In some examples, the system may compare curves from different probability to void functions determined over time. In other examples, the comparison may look at changes to a coefficient and/or variable that defines the different probability to void functions. In any case, the system may use some technique to compare probability to void functions that may be graphical and/or mathematical in nature.

Figure 12:
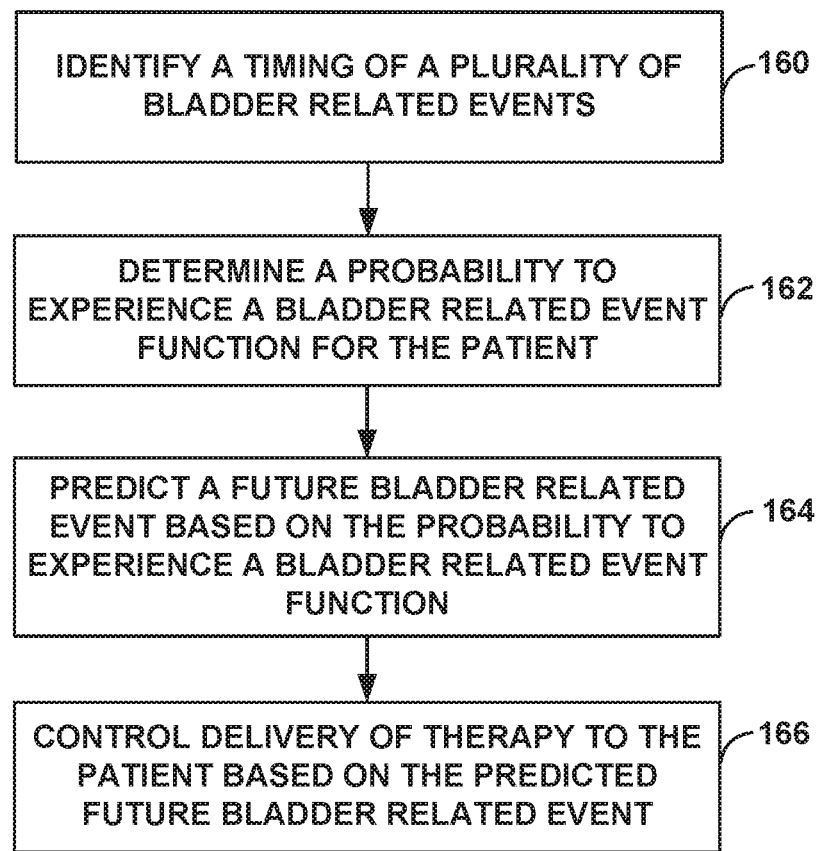
FIG. 12 is a flow diagram illustrating an example technique for determining a probability to experience a bladder related event function for a patient.

FIG. 12 is a flow diagram illustrating an example technique of determining a probability to experience a bladder related event function for a patient. The technique of FIG. 12 will be described with respect to system 10 of FIG. 1. In other examples, however, the technique of FIG. 12 may be used with a system other than system 10 of FIG. 1, such as by patient programmer 22 or a networked server or other device and/or system.

In some examples, processing circuitry 32 of IMD 14 identifies a timing of a plurality of bladder related events (160). In some examples, patient 12 may input the timing of a bladder related event using a user input device, such as a patient programmer 22, and the timing of the bladder related event may be transmitted to IMD 14, e.g., via a network. Additionally, or alternatively, system 10 may include one or more sensors configured to identify the timing of a plurality of bladder related events of patient 12. For example, system 10 may include a sensor configured to determine a volume of the bladder of patient 12 (e.g., impedance sensing via the bladder), a pressure of the bladder, a physical activity of patient 12, or the like. In some such examples, the one or more sensors may be included IMD 14 or lead 16. In other examples, the one or more sensors may be separate from IMD 14 and/or lead 16, but may be in communication, e.g., via a network, with IMD 14, lead 16, patient programmer 22, or a clinician programmer 20. In some examples, the timing of the plurality of bladder related events may be identified by a geofence associated with a bathroom and/or a toilet.

The technique of FIG. 12 further includes processing circuitry 32 of IMD 14 determining a probability to experience a bladder related event function for the patient (162). The probability to experience a bladder related event function may be based on the timing of the plurality of bladder related events, and may include an instantaneous probability to experience a bladder related event function or a cumulative probability to experience a bladder related event function that indicates a probability that patient 12 will experience a bladder related event at an elapsed time after a previous bladder related event. As one example, IMD 14 may select a composite probability to experience a bladder related event function based on a plurality of subjects and based on one or more parameters of patient 12, such as an age, a gender, and/or a body composition of patient 12. IMD 14 may then adjust the composite probability to experience a bladder related event function based on the plurality of subjects based on the timing of the plurality of bladder related events. As another example, IMD 14 may determine the probability to experience a bladder related event function for patient 12 may be based on at least one of a pressure of the bladder of patient 12, a volume of the bladder of patient 12, a physical activity of patient 12, a time of day, an amount of fluid intake of patient 12, or an amount of caffeine consumed by patient 12.

After determining the probability to experience a bladder related event function (162), processing circuitry 32 predicts a future bladder related event based on the probability to experience a bladder related event function (164). For example, an instantaneous probability to experience a bladder related event function or a cumulative to void function may indicate the timing of a future bladder related event based on the probability a future bladder related event will occur from an occurrence of a previous bladder related event. In some examples, processing circuitry 32 may determine when the probability exceeds a threshold and identify the corresponding time from the previous bladder related event as the time for the predicted future bladder related event.

In some examples, IMD 14 may detect a urinary condition of patient 12 based on the probability to experience a bladder related event function. For example, IMD 14 diagnose a urinary condition of patient 12 if the probability to experience a bladder related event function for patient 12 is determined to be similar to a composite probability to experience a bladder related event function based on a plurality of subjects that exhibit a certain condition or urinary disorder.

The technique of FIG. 12 also includes processing circuity 32 controlling IMD 14 to deliver therapy to patient 12 based on the predicted timing of the future bladder related event (166). The therapy delivered to patient 12 may be configured to modulate activity of nerves and/or muscles associated with the bladder of patient in order to reduce symptoms associated the bladder dysfunction of patient 12, such as, for example, overactive bladder, urinary incontinence, urinary retention, or other symptoms associated with bladder dysfunction of patient 12.

In other cases, another device, such as programmer 22 may control IMD 14 to delivery therapy according to the predicted timing of the future bladder related event. In some examples, processing circuitry 32 may indicate that therapy is being delivered or will be delivered via programmer 22. In some examples, programmer 22 may display a prompt to the user to reject delivery of therapy (e.g., when the patient desires to void or experience another bladder related event) or prompt the user to confirm that therapy should be delivered. In alternative examples, a system may display when the predicted bladder related event will occur without providing therapy. Such a system may just be an external device that receives input from the user and suggests to the user when the next bladder related event may occur based on the determined probability to experience a bladder related event function.

Figure 13:
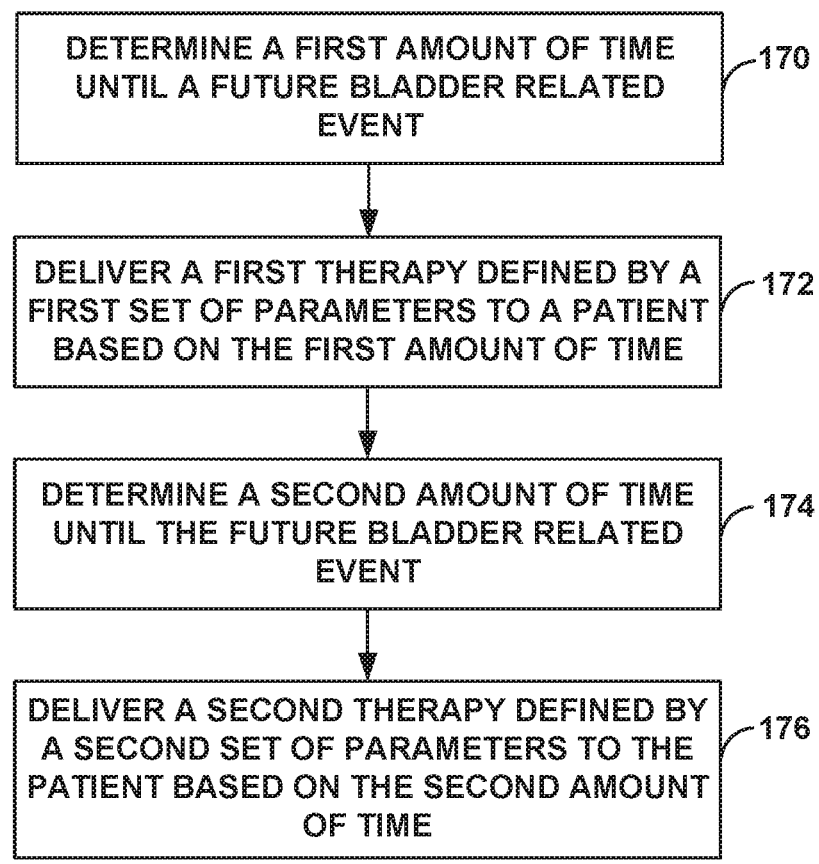
FIG. 13 is a flow diagram illustrating an example technique of delivering therapy to a patient.

FIG. 13 is a flow diagram illustrating an example technique of delivering therapy to a patient. The technique of FIG. 13 will be described with respect to system 10 of FIG. 1. In other examples, however, the technique of FIG. 13 may be used with a system other than system 10 of FIG. 1, such as by programmer 22, a networked server or other device and/or system.

In some examples, IMD 14 delivers therapy to patient 12. For example, delivering therapy to patient 12 may include processing circuitry 32 of IMD 14 determining a first amount of time until a future bladder related event (170) and delivering a first therapy defined by a first set of parameter values to patient 12 based on the first amount of time until the future bladder related event (172). As one example, the first therapy may be delivered based on a first amount of time corresponding to 25% of the timing of the predicted future bladder related event (e.g., 25% of the time to the predicted future bladder related event has elapsed from the last bladder related event). IMD 14 may then determine a second amount of time until the future bladder related event (174) and deliver a second therapy with a second set of parameter values to patient 12 based on the second amount of time until the future bladder related event (176). For example, the second therapy may be delivered based on a second amount of time corresponding to 50% of the timing of the predicted future bladder related event (e.g., 50% of the time to the predicted future bladder related event has elapsed from the last bladder related event). The second set of parameter values may be the same as or different from the first set of parameter values. In other examples, other percentages or other amounts of time other than a percentage of time until the future bladder related event may be used to deliver first and second therapies to the patient. The system may employ more than two amounts of times in other examples to further refine delivery of therapy. In addition, in other examples, the first amount of time and the second amount of time may be determined prior to delivering the first therapy at the first amount of time.

In some examples, different sets of parameter values may benefit patient 12 at different times. For example, at a first amount of time until the predicted future bladder related event that is greater than the second amount of time until the future bladder related event, patient 12 may benefit from reduced or less intense therapy (e.g., lower voltage or current amplitude values) than at times closer to the predicted timing of the future bladder related event, such as the second amount of time until the future bladder related event. In other examples, the first and second set of parameter values may differ from each other in a parameter other than, or in addition to, a parameter that defines the intensity of the therapy.

Figure 14:
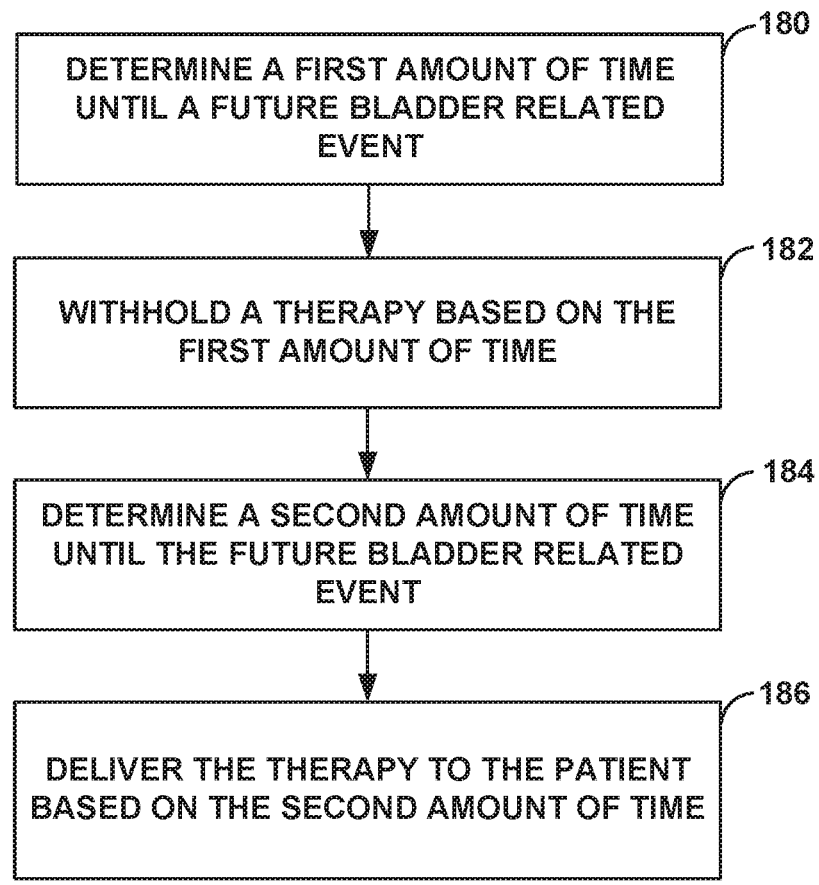
FIG. 14 is a flow diagram illustrating another example technique of delivering therapy to a patient.

FIG. 14 is a flow diagram illustrating another example technique of delivering therapy to a patient. The technique of FIG. 14 will be described with respect to system 10 of FIG. 1. In other examples, however, the technique of FIG. 14 may be used with a system other than system 10 of FIG. 1, such as by programmer 22, a networked server or other device and/or system.

In some examples, patient 12 may benefit from receiving no therapy during certain times during a bladder fill cycle. In this manner, system 10 may withhold the delivery of therapy based on an amount of time until the predicted future bladder related event. For example, based on a probability to experience a bladder related event function for patient 12, processing circuitry 32 of IMD 14 determines a first amount of time until a future bladder related event (180). This first amount of time may start at the end of the previous bladder related event and run until a second amount of time until a future bladder related event. Processing circuitry 32 then withholds delivery of any therapy based on the first amount of time until the future bladder related event (182). In some such examples, it may be desirable to withhold therapy at certain amount of times from the predicted bladder related event, such as if the probability to experience the bladder related event is relatively low (e.g., the patient is unlikely to have a bladder related event because the previous bladder related event is relatively recent) at the first amount of time until the future bladder related event.

Processing circuitry 32 also determines a second amount of time until the future bladder related event (184) to determine when to deliver the therapy to patient 12. In addition, in other examples, the first amount of time and the second amount of time may be determined prior to delivering the first therapy at the first amount of time. In response to determining that the system has entered the second amount of time until the future bladder related event, processing circuitry 32 delivers the therapy to patient 12 based on the second amount of time until the future bladder related event (186). In some cases, the second amount of time until the predicted future bladder related event may be less than the first amount of time until the predicted future bladder related event. Put another way, the first amount of time occurs prior to the second amount of time, so the first amount of time until the predicted future bladder related event is a greater amount of time until the predicted future bladder related event than the second amount of time until the future bladder related event. An alternative approach to tracking the first and second amount of time until predicted future bladder related event is determined elapsed times from the previous bladder related event and withhold or delivery therapy between these elapsed times. For example, processing circuitry 32 may withhold therapy for a first period of time starting at the previous bladder related event and ending at an elapsed time from the previous bladder related event that marks the start of a second period of time that runs until the predicted future bladder related event, where system 10 delivers therapy during the second period of time. In other examples, three or more periods of time may be tracked between consecutive bladder related events and used to determine when to withhold therapy or what type of therapy to deliver during the respective time periods.

Figure 15:
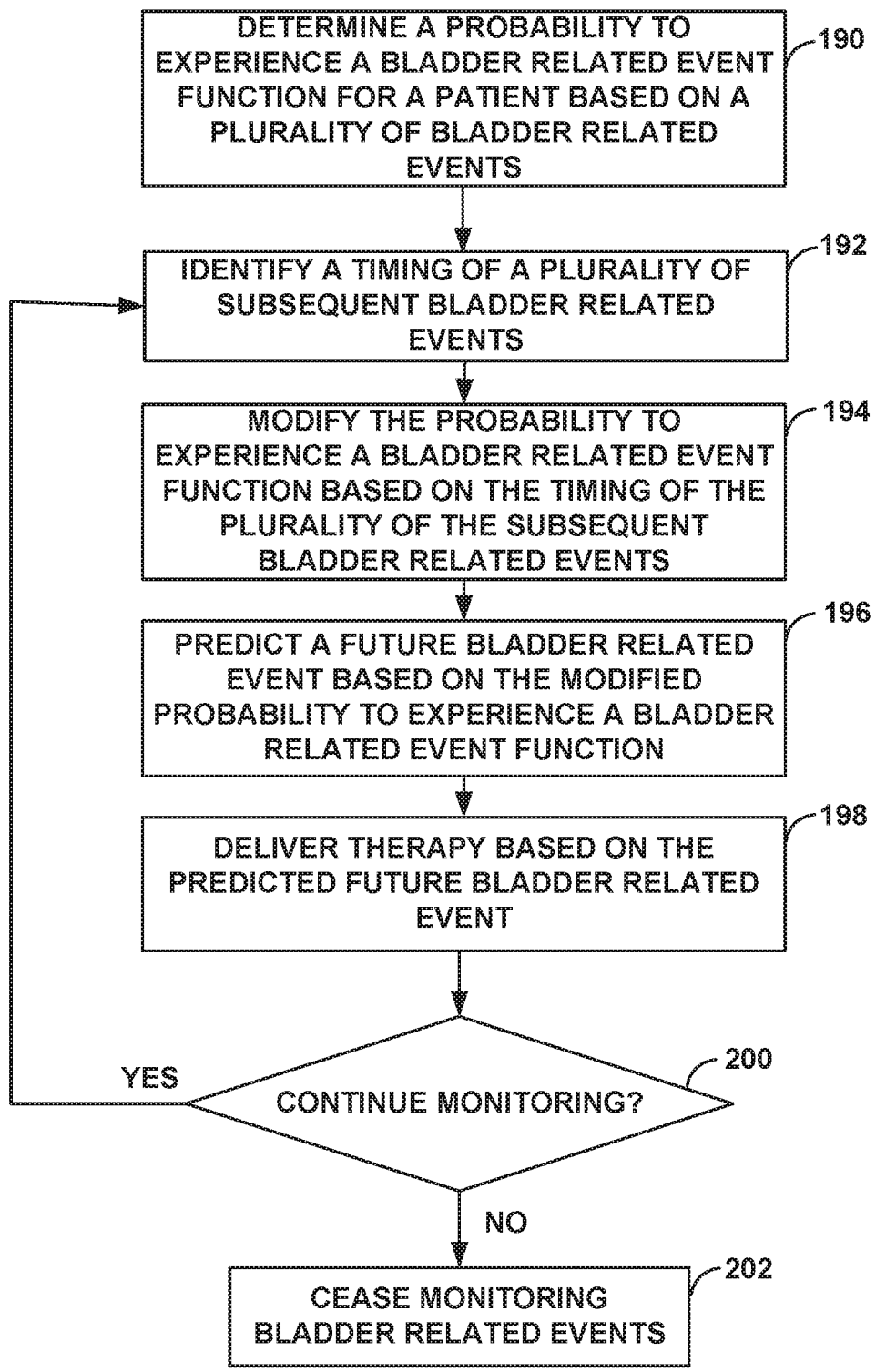
FIG. 15 is a flow diagram illustrating an example technique of modifying a probability to experience a bladder related event function of a patient.

FIG. 15 is a flow diagram illustrating an example technique of modifying a probability to experience a bladder related event function for a patient. The technique of FIG. 15 will be described with respect to system 10 of FIG. 1. In other examples, however, the technique of FIG. 15 may be used with a system other than system 10 of FIG. 1, such as by programmer 22, a networked server, or other device and/or system.

Processing circuitry 32 of IMD 14 may be configured to determine a probability to experience a bladder related event function for a patient based on a plurality of bladder related events (190). After this probability to experience a bladder related event function is determined, processing circuitry 32 may continue to update the probability to experience a bladder related event function or generate new probability to experience a bladder related event functions that better reflect the current patient condition. For example, processing circuitry 32 may continue to identify a timing of a plurality of subsequent bladder related events of patient 12 (192). IMD 14 may deliver therapy, in some examples, during the same time in which these subsequent bladder related events of patient 12 are identified. IMD 14 then modifies the probability to experience a bladder related event function for patient 12 based on the timing of the plurality of subsequent bladder related events (194). As one example, the probability to experience a bladder related event function may be modified by shifting the curve of the probability to experience a bladder related event function to the right, such as in the case in which the therapy decreased overactivity of the bladder and/or urinary incontinence of patient 12. In other examples, the probability to experience a bladder related event function for patient 12 may be modified in another way based on the timing of the plurality of subsequent bladder related events. Processing circuitry 32 may continually modify the probability to experience a bladder related event function after each identified bladder related event, after a certain number of identified bladder related events occur, after a certain period of time elapsing since the last probability to experience a bladder related event function was determined, or at other periodic times. Instead of modifying the probability to experience a bladder related event function, processing circuitry 32 may generate a new probability to experience a bladder related event function that replaces the previous probability to experience a bladder related event function for use in delivering therapy. Previous probability to experience a bladder related event functions may be stored for comparison or other analysis regarding changes to the patient over time.

Using the modified probability to experience a bladder related event function, processing circuitry 32 of IMD 14 may predict a future bladder related event based on the modified probability to experience a bladder related event function (196) and deliver therapy to the patient based on the predicted future bladder related event (198). In some examples, processing circuitry 32 may adjust the time at which therapy is delivered based on the future bladder related event predicted from the modified probability to experience a bladder related event function. In addition, or alternatively, processing circuitry 32 may modify at least one parameter value of the set of therapy parameter values that define the therapy based on at least one of the predicted bladder related event or the modified probability to experience a bladder related event function. For example, processing circuitry 32 may decrease voltage or current amplitude of electrical stimulation if the probability to experience a bladder related event function has shifted to the right (e.g., symptoms of bladder dysfunction have improved). As another example, processing circuitry 32 may increase the intensity and/or the duration of the therapy (e.g., longer pulse widths and/or beginning therapy sooner after a bladder related event) in some cases in which the probability to experience a bladder related event function for the patient was shifted to the left (e.g., overactivity of the bladder and/or urinary incontinence was increased). IMD 14 may then deliver the modified therapy to patient 12 based on the second future bladder related event (198).

If processing circuitry 32 has instructions to continue monitoring bladder related events of the patient ("YES" branch of block 200), processing circuitry 32 will continue to identify timing of subsequent bladder related events (192) and modify the probability to experience a bladder related event function (194). If processing circuitry 32 has instructions to stop monitoring bladder related events of the patient ("NO" branch of block 200), processing circuitry 32 will cease monitoring subsequent bladder related events for modifying the probability to experience a bladder related event function of the patient (202). In some examples, even if processing circuitry 32 is no longer tracking bladder related events to modify or update the probability to experience a bladder related event function, processing circuitry 32 may still continue to control therapy delivery based on the current probability to experience a bladder related event function.

Figure 16:
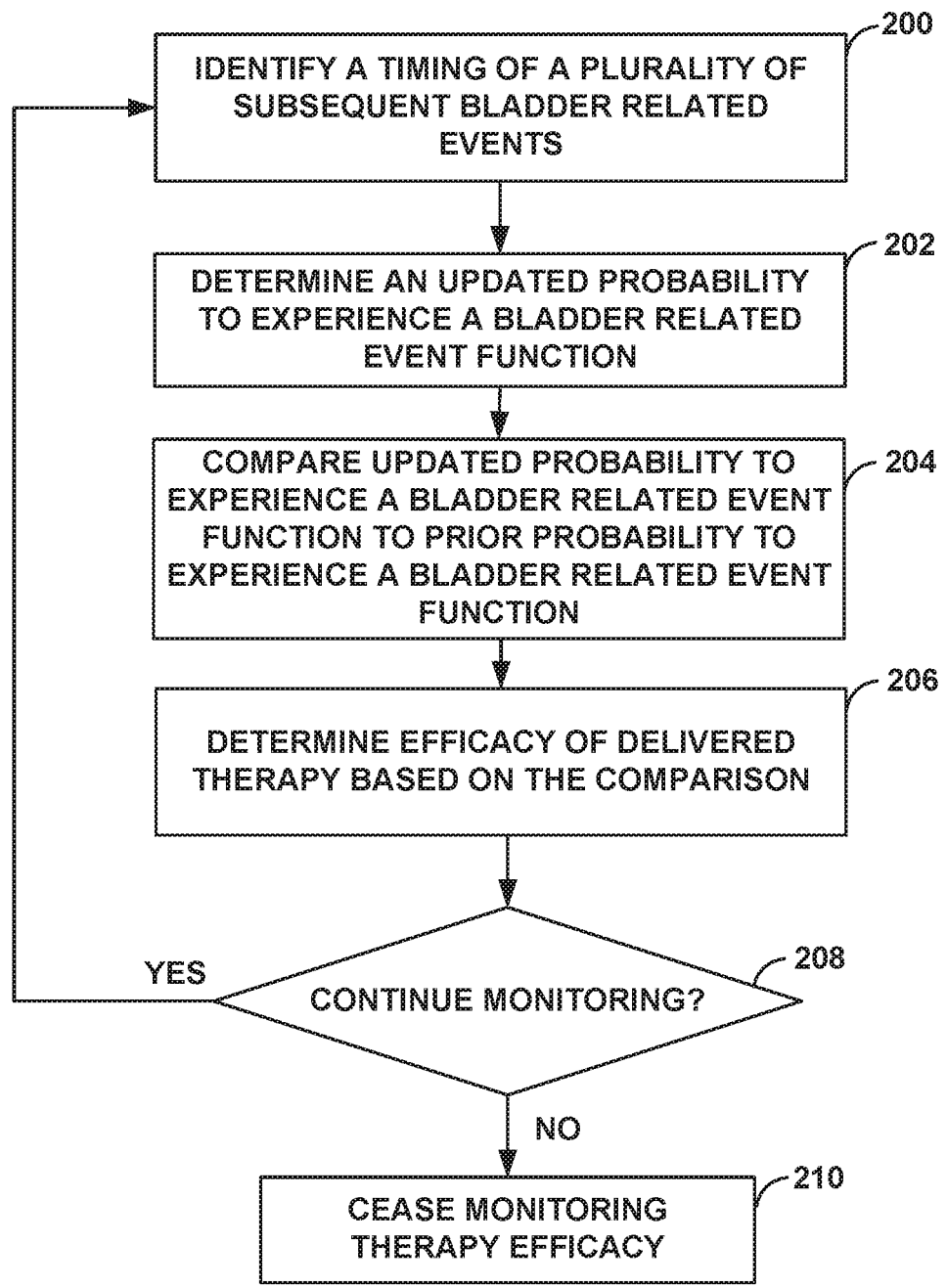
FIG. 16 is a flow diagram illustrating an example technique for determining an efficacy of therapy delivered to a patient.

FIG. 16 is a flow diagram illustrating another example technique of determining an efficacy of therapy delivered to a patient. The technique of FIG. 16 will be described with respect to system 10 of FIG. 1. In other examples, however, the technique of FIG. 16 may be used with a system other than system 10 of FIG. 1, such as by programmer 22, a networked server, or other device and/or system.

Processing circuitry 32 of IMD 14 may be configured to determine a probability to experience a bladder related event function for a patient based on a plurality of bladder related events (e.g., according to the process of FIG. 12) or otherwise receive a probability to experience a bladder related event function for the patient. Processing circuitry 32 may then identify a timing of a plurality of subsequent bladder related events of patient 12 (200). Processing circuitry 32 then modifies the probability to experience a bladder related event function for patient 12 based on the timing of the plurality of subsequent bladder related events (202). This modified probability to experience a bladder related event function may be an updated or new probability to experience a bladder related event function for the patient. In response to determining the updated probability to experience a bladder related event function for the patient, processing circuitry 32 may compare the updated probability to experience a bladder related event function to a prior probability to experience a bladder related event function for the patient (204). For example, the updated probability to experience a bladder related event function may be compared to the previously determined probability to experience a bladder related event function, an older probability to experience a bladder related event function of the patient (e.g., a probability to experience a bladder related event function determined prior to any therapy delivered to the patient), or a composite probability to experience a bladder related event function (e.g., a composite probability to experience a bladder related event function indicating a "normal" probability to experience a bladder related event function for a plurality of subjects without the bladder dysfunction or a composite probability to experience a bladder related event function for subjects suffering from bladder dysfunction, such as urinary retention, overactive bladders, urinary incontinence, or another bladder dysfunction).

The comparison may include determining whether the updated probability to experience a bladder related event function is a curve that is shifted left or right to identify whether or not therapy is reducing symptoms for the patient. In this manner, processing circuitry 32 may determine efficacy of previously delivered therapy based on the comparison of probability to experience a bladder related event functions (206). Processing circuitry 32 may maintain therapy or adjust therapy based on whether or not therapy has been effective to treat patient 12.

If processing circuitry 32 has instructions to continue monitoring bladder related events of the patient ("YES" branch of block 208), processing circuitry 32 will continue to identify timing of subsequent bladder related events (200) and modify the probability to experience a bladder related event function (202). If processing circuitry 32 has instructions to stop monitoring bladder related events of the patient ("NO" branch of block 208), processing circuitry 32 will cease monitoring therapy efficacy (210). In some examples, even if processing circuitry 32 is no longer tracking therapy efficacy, processing circuitry 32 may still continue to control therapy delivery based on the current or updated probability to experience a bladder related event functions.

Although FIGS. 12-16 were described with respect to IMD 14, and the processing circuitry of IMD 14, in other examples, one or more additional devices, components, processing circuitry, or any combination thereof, may perform one or more steps of any of the techniques described herein. Moreover, the techniques of FIGS. 12-16 may be implemented in any order, may be implemented simultaneously, may have one or more steps added and/or deleted, and may be implemented in combination with one another.

The techniques described in this disclosure, including those attributed to system 10, IMD 14, patient programmer 22, and clinician programmer 20, and various constituent components, may be implemented, at least in part, in hardware, software, firmware or any combination thereof. For example, various aspects of the techniques may be implemented within one or more processors or processing circuitry, including one or more microprocessors, DSPs, ASICs, FPGAs, or any other equivalent integrated or discrete logic circuitry, as well as any combinations of such components, remote servers, remote client devices, or other devices. The term "processor" or "processing circuitry" may generally refer to any of the foregoing logic circuitry, alone or in combination with other logic circuitry, or any other equivalent circuitry.

Such hardware, software, firmware may be implemented within the same device or within separate devices to support the various operations and functions described in this disclosure. In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

The techniques or processes described in this disclosure may also be embodied or encoded in an article of manufacture including a computer-readable storage medium encoded with instructions. Instructions embedded or encoded in an article of manufacture including a computer-readable storage medium encoded, may cause one or more programmable processors, or other processors, to implement one or more of the techniques described herein, such as when instructions included or encoded in the computer-readable storage medium are executed by the one or more processors. Example computer-readable storage media may include random access memory (RAM), read only memory (ROM), programmable read only memory (PROM), erasable programmable read only memory (EPROM), electronically erasable programmable read only memory (EEPROM), flash memory, a hard disk, a compact disc ROM (CD-ROM), a floppy disk, a cassette, magnetic media, optical media, or any other computer readable storage devices or tangible computer readable media. The computer-readable storage medium may also be referred to as storage devices.

In some examples, a computer-readable storage medium comprises non-transitory medium. The term "non-transitory" may indicate that the storage medium is not embodied in a carrier wave or a propagated signal. In certain examples, a non-transitory storage medium may store data that can, over time, change (e.g., in RAM or cache).

Various examples have been described herein. Any combination of the described operations or functions is contemplated. These and other examples are within the scope of the following claims.

What is claimed is:

1. A method comprising:
   identifying a timing of a plurality of bladder related events of a patient, wherein the plurality of bladder related events comprises at least one of a voiding event or bladder related events that occurred prior to the voiding event;
   determining, based on the timing of the plurality of bladder related events of the patient, a probability to experience a bladder related event function for the patient, the probability to experience a bladder related event function indicating a probability that the patient will experience a subsequent bladder related event at an elapsed time after a previous bladder related event;

predicting, based on the probability to experience a bladder related event function, a timing of a future bladder related event, wherein the future bladder related event occurs after the voiding event; and controlling delivery of a therapy to the patient based on the predicted timing of the future bladder related event.

2. The method of claim 1, wherein the future bladder related event comprises a future void event, and wherein the probability to experience a bladder related event function comprises a probability to void function.

3. The method of claim 2, wherein the probability to void function comprises an instantaneous probability to void function or a cumulative probability to void function.

4. The method of claim 2, further comprising delivering the therapy to the patient based on the predicted timing of the future void event.

5. The method of claim 4, wherein delivering the therapy to the patient based on the predicted timing of the future void event comprises:
    determining a first amount of time until the future void event;
    delivering a first therapy defined by a first set of parameters to the patient based on the first amount of time until the future void event;
    determining a second amount of time until the future void event; and
    delivering a second therapy defined by a second set of parameters to the patient based on the second amount of time until the future void event, wherein the first amount of time is greater than the second amount of time.

6. The method of claim 4, wherein delivering the therapy to the patient based on the predicted timing of the future void event comprises:
    determining a first amount of time until the future void event or related symptom;
    determining a second amount of time until the future void event or related symptom, the first amount of time being greater than the second amount of time;
    withholding the therapy during the first amount of time until the future void event and until the second amount of time until the future void event occurs; and
    delivering the therapy to the patient during the second amount of time until the future void event.

7. The method of claim 4, wherein the plurality of bladder related events comprises a first plurality of voiding events, the future void event comprises a first future void event, the therapy comprises a first therapy, and wherein the method further comprises:
    after delivering the therapy to the patient, identifying a timing of a second plurality of bladder voiding events of the patient;
    modifying, based on the timing of the second plurality of bladder voiding events, the probability to void function;
    predicting, based on the modified probability to void function, a timing of a second future void event; and
    delivering a second therapy to the patient based on the timing of the second future void event.

8. The method of claim 2, wherein the probability to void function comprises a first probability to void function and the plurality of bladder related events comprises a first plurality of bladder voiding events, and wherein the method further comprises:
    after delivery of the therapy to the patient, identifying a timing of a second plurality of bladder voiding events of the patient;
    determining, based on the timing of the second plurality of bladder voiding events of the patient, a second probability to void function for the patient; and
    determining, based on the second probability to void function, an efficacy of the therapy delivered to the patient.

9. The method of claim 8, wherein determining the efficacy of the therapy comprises at least one of:
    comparing the first probability to void function to the second probability to void function; or
    comparing the second probability to void function to a composite probability to void function based on a plurality of subjects.

10. The method of claim 2, further comprising detecting a urinary condition of the patient by comparing the probability to void function of the patient to a composite probability to void function based on a plurality of subjects.

11. The method of claim 2, wherein identifying the timing of the plurality of bladder related events of the patient comprises at least one of:
    receiving, via a network, user input entered by the patient via a user interface device;
    receiving, via the network, pressure data from a first sensor configured to measure a pressure of the bladder of the patient;
    receiving, via the network, volume data from a second sensor configured to measure a volume of the bladder of the patient; or
    receiving, via the network, physical activity data from a third sensor configured to detect a physical activity of the patient.

12. The method of claim 2, wherein determining the probability to void function of the patient comprises:
    selecting a composite probability to void function based on a plurality of subjects and based on at least one of:
        an age of the patient;
        a gender of the patient; or
        a body composition of the patient; and
    modifying, based on the timing of the plurality of bladder related events of the patient, the composite probability to void function based on the plurality of subjects to generate the probability to void function of the patient.

13. The method of claim 2, wherein determining the probability to void function comprises determining the probability to void function based on at least one of:
    a pressure of the bladder of the patient;
    a volume of the bladder of the patient;
    a physical activity of the patient;
    a time of day;
    an amount of fluid intake of the patient; or
    an amount of caffeine consumed by the patient.

14. A system comprising:
    processing circuitry configured to:
        identify a timing of a plurality of bladder related events of a patient, wherein the plurality of bladder related events comprises at least one of a voiding event or bladder related events that occurred prior to the voiding event;
        determine, based on the timing of the plurality of bladder related events of the patient, a probability to experience a bladder related event function for the patient, the probability to experience a bladder related event function indicating a probability that the patient will experience a subsequent bladder related event at an elapsed time after a previous bladder related event;

predict, based on the probability to experience a bladder related event function, a timing of a future bladder related event, wherein the future bladder related event occurs after the voiding event; and control delivery of a therapy to the patient based on the predicted timing of the future bladder related event.

15. The system of claim 14, wherein the future bladder related event comprises a future void event, and wherein the probability to experience a bladder related function comprises a probability to void function.

16. The system of claim 15, wherein the probability to void function comprises an instantaneous probability to void function or a cumulative probability to void function.

17. The system of claim 16, further comprising a stimulation delivery module configured to deliver the therapy to the patient based on the predicted timing of the future void event.

18. The system of claim 17, wherein, to deliver the therapy to the patient based on the predicted timing of the future void event, the processing circuitry is further configured to:

determine a first amount of time until the future void event;

deliver a first therapy defined by a first set of parameters to the patient based on the first amount of time until the future void event;

determine a second amount of time until the future void event; and control the stimulation delivery module to deliver a second therapy defined by a second set of parameters to the patient based on the second amount of time until the future void event, wherein the first amount of time is greater than the second amount of time.

19. The system of claim 17, wherein, to deliver the therapy to the patient based on the predicted timing of the future void event, the processing circuitry is further configured to:

determine a first amount of time until the future void event;

determine a second amount of time until the future void event, the first amount of time being greater than the second amount of time;

withhold the therapy during the first amount of time until the future void event and until the second amount of time until the future void event occurs; and control the stimulation delivery module to deliver the therapy to the patient based on the second amount of time until the future void event.

20. The system of claim 17, wherein the plurality of bladder related events comprises a first plurality of voiding events, the future void event comprises a first future void event, the therapy comprises a first therapy, and wherein the processing circuitry is further configured to:

after delivery of the therapy to the patient, identify a timing of a second plurality of bladder voiding events of the patient;

modify, based on the timing of the second plurality of bladder voiding events, the probability to void function;

predict, based on the modified probability to void function, a timing of a second future void event; and control the stimulation delivery module to deliver a second therapy to the patient based on the timing of the second future void event.

21. The system of claim 17, wherein the probability to void function comprises a first probability to void function and the plurality of bladder related events comprises a first plurality of bladder voiding events, and wherein the processing circuitry is further configured to:

after delivery of the therapy to the patient, identify a timing of a second plurality of bladder voiding events of the patient;

determine, based on the timing of the second plurality of bladder voiding events of the patient, a second probability to void function for the patient; and determine, based on the second probability to void function, an efficacy of the therapy delivered to the patient.

22. The system of claim 21, wherein determining the efficacy of the therapy comprises at least one of:

comparing the first probability to void function to the second probability to void function; or comparing the second probability to void function to a composite probability to void function based on a plurality of subjects.

23. The system of claim 15, wherein the processing circuitry is configured to detect a urinary condition of the patient by comparing the probability to void function to a composite probability to void function based on a plurality of subjects.

24. The system of claim 15, wherein the processing circuitry is configured to identify the timing of the plurality of bladder related events of the patient by at least one of:

receiving, via a network, user input entered by the patient via a user interface device;

receiving, via the network, pressure data from a first sensor configured to measure a pressure of the bladder of the patient;

receiving, via the network, volume data from a second sensor configured to measure a volume of the bladder of the patient; or receiving, via the network, physical activity data from a third sensor configured to detect a physical activity of the patient.

25. The system of claim 15, wherein the processing circuitry is configured to determine the probability to void function of the patient by:

selecting a composite probability to void function based on a plurality of subjects and based on at least one of:

an age of the patient;

a gender of the patient; or a body composition of the patient; and modifying, based on the timing of the plurality of bladder related events of the patient, the composite probability to void function based on the plurality of subjects to generate the probability to void function of the patient.

26. The system of claim 15, wherein the processing circuitry is configured to determine the probability to void function of the patient based on at least one of:

a pressure of the bladder of the patient;

a volume of the bladder of the patient;

a physical activity of the patient;

a time of day;

an amount of fluid intake of the patient; or an amount of caffeine consumed by the patient.

27. The system of claim 15, further comprising a sensor configured to detect the plurality of bladder related events of the patient.

28. The system of claim 15, further comprising an implantable medical device comprising the processing circuitry.

29. A computer readable storage medium comprising instructions that, when executed, causes processing circuitry to:
- identify a timing of a plurality of bladder related events of a patient, wherein the plurality of bladder related events comprises at least one of a voiding event or bladder related events that occurred prior to the voiding event;
- determine, based on the timing of the plurality of bladder related events of the patient, a probability to experience a bladder related event function for the patient, the probability to experience a bladder related event function indicating a probability that the patient will experience a subsequent bladder related event at an elapsed time after a previous bladder related event;
- predict, based on the probability to experience a bladder related event function, a timing of a future bladder related event, wherein the future bladder related event occurs after the voiding event; and
- control delivery of a therapy to the patient based on the predicted timing of the future bladder related event.

* * * * *